(12) United States Patent
Palinsky et al.

(10) Patent No.: US 11,242,372 B2
(45) Date of Patent: Feb. 8, 2022

(54) IFN BETA PROTEIN ANALOGS

(71) Applicant: ARES TRADING S.A., Aubonne (CH)

(72) Inventors: Wolf Palinsky, Belmont sur Lausanne (CH); Mara Rossi, Rome (IT); Anna R. Pezzotti, Rome (IT)

(73) Assignee: ARES TRADING S.A., Aubonne (CH)

( * ) Notice: Subject to any disclaimer, the term of this patent is extended or adjusted under 35 U.S.C. 154(b) by 765 days.

(21) Appl. No.: 16/116,964

(22) Filed: Aug. 30, 2018

(65) Prior Publication Data

US 2018/0362609 A1 Dec. 20, 2018

Related U.S. Application Data

(62) Division of application No. 15/300,288, filed as application No. PCT/EP2015/057205 on Apr. 1, 2015, now abandoned.

(30) Foreign Application Priority Data

Apr. 4, 2014 (EP) .................................... 14163483

(51) Int. Cl.
   *C07K 14/565* (2006.01)
   *A61K 38/00* (2006.01)

(52) U.S. Cl.
   CPC ............ *C07K 14/565* (2013.01); *A61K 38/00* (2013.01)

(58) Field of Classification Search
   CPC ...... A61K 38/00; A61K 38/21; A61K 38/215; C07K 14/565; C07K 1/14; C07K 1/34
   See application file for complete search history.

(56) References Cited

U.S. PATENT DOCUMENTS

| 8,993,724 B2 | 3/2015 | Fischer et al. |
| 2007/0292391 A1 | 12/2007 | Samaritani et al. |
| 2008/0219952 A1 | 9/2008 | Fischer et al. |
| 2011/0305669 A1 | 12/2011 | Fischer et al. |
| 2012/0082647 A1 | 4/2012 | Baker et al. |

FOREIGN PATENT DOCUMENTS

| WO | WO 2006/049423 | 5/2006 |
| WO | WO 2006/053134 | 5/2006 |
| WO | WO 2007/022799 | 3/2007 |
| WO | WO 2008/020968 | 2/2008 |

OTHER PUBLICATIONS

Cabra, V., et al. Effect of alkaline deamidation on the structure, surface hydrophobicity, and emulsifying properties of the Z19 alpha-zein. Journal of Agricultural and Food Chemistry, 2007, 55:439-445.*
Kato, A., et al. Deamidation of food proteins by proteases in alkaline pH. Journal of Agricultural and Food Chemistry, 1987, 35:224-227.*
Conradt, H. S. et al. "Structure of the Carbohydrate Moiety of Human Interferon-β Secreted by a Recombinant Chinese Hamster Ovary Cell Line" *The Journal of Biological Chemistry*, Oct. 25, 1987, p. 14600-14605, vol. 262, No. 30.
Written Opinion in International Application No. PCT/EP2015/057205, dated May 30, 2016, pp. 1-7.
Jacobs, L. D. et al. "Intramuscular Interferon Beta-la for Disease Progression in Relapsing Multiple Sclerosis" *Annals of Neurology*, Mar. 1996, pp. 285-294, vol. 39, No. 3.
Nakajima, H. et al. "Enhanced tumor immunity of WT1 peptide vaccination by interferon-β administration" *Vaccine*, 2012, pp. 722-729, vol. 30.

* cited by examiner

*Primary Examiner* — Prema M Mertz
(74) *Attorney, Agent, or Firm* — Saliwanchik, Lloyd & Eisenschenk

(57) ABSTRACT

The present invention provides a composition comprising an interferon-beta (IFN-beta) protein of which at least 80% is deamidated, a deamidated IFN-beta 1a protein, methods of producing deamidated proteins, and therapeutic uses of such compositions and deamidated IFN-beta 1a proteins.

5 Claims, 25 Drawing Sheets
(23 of 25 Drawing Sheet(s) Filed in Color)
Specification includes a Sequence Listing.

Figure 1A: r-hIFN-β-1a amino-acidic sequence

| 1 | | | | | | | | | 10 | | | | | | | | | | 20 |
|---|---|---|---|---|---|---|---|---|---|---|---|---|---|---|---|---|---|---|---|
| M | S | Y | N | L | L | G | F | L | Q | R | S | S | N | F | Q | C | Q | K | L |
| | | | | | | | | | 30 | | | | | | | | | | 40 |
| L | W | Q | L | N | G | R | L | E | Y | C | L | K | D | R | M | N | F | D | I |
| | | | | | | | | | 50 | | | | | | | | | | 60 |
| P | E | E | I | K | Q | L | Q | Q | F | Q | K | E | D | A | A | L | T | I | Y |
| | | | | | | | | | 70 | | | | | | | | | | 80 |
| E | M | L | Q | N | I | F | A | I | F | R | Q | D | S | S | S | T | G | W | N |
| | | | | | | | | | 90 | | | | | | | | | | 100 |
| E | T | I | V | E | N | L | L | A | N | V | Y | H | Q | I | N | H | L | K | T |
| | | | | | | | | | 110 | | | | | | | | | | 120 |
| V | L | E | E | K | L | E | K | E | D | F | T | R | G | K | L | M | S | S | L |
| | | | | | | | | | 130 | | | | | | | | | | 140 |
| H | L | K | R | Y | Y | G | R | I | L | H | Y | L | K | A | K | E | Y | S | H |
| | | | | | | | | | 150 | | | | | | | | | | 160 |
| C | A | W | T | I | V | R | V | E | I | L | R | N | F | Y | F | I | N | R | L |
| | | | | | 166 | | | | | | | | | | | | | | |
| T | G | Y | L | R | N | | | | | | | | | | | | | | |

Figure 1B: Schematic representation of the r-hIFN-β-1a structure
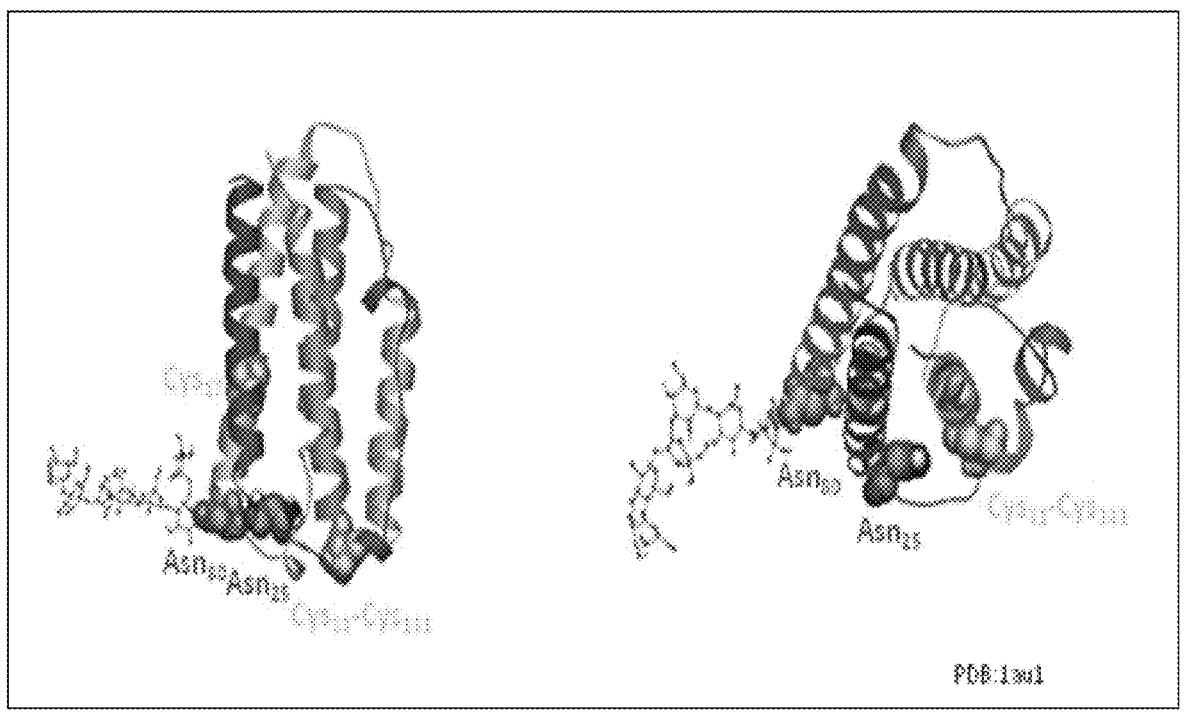

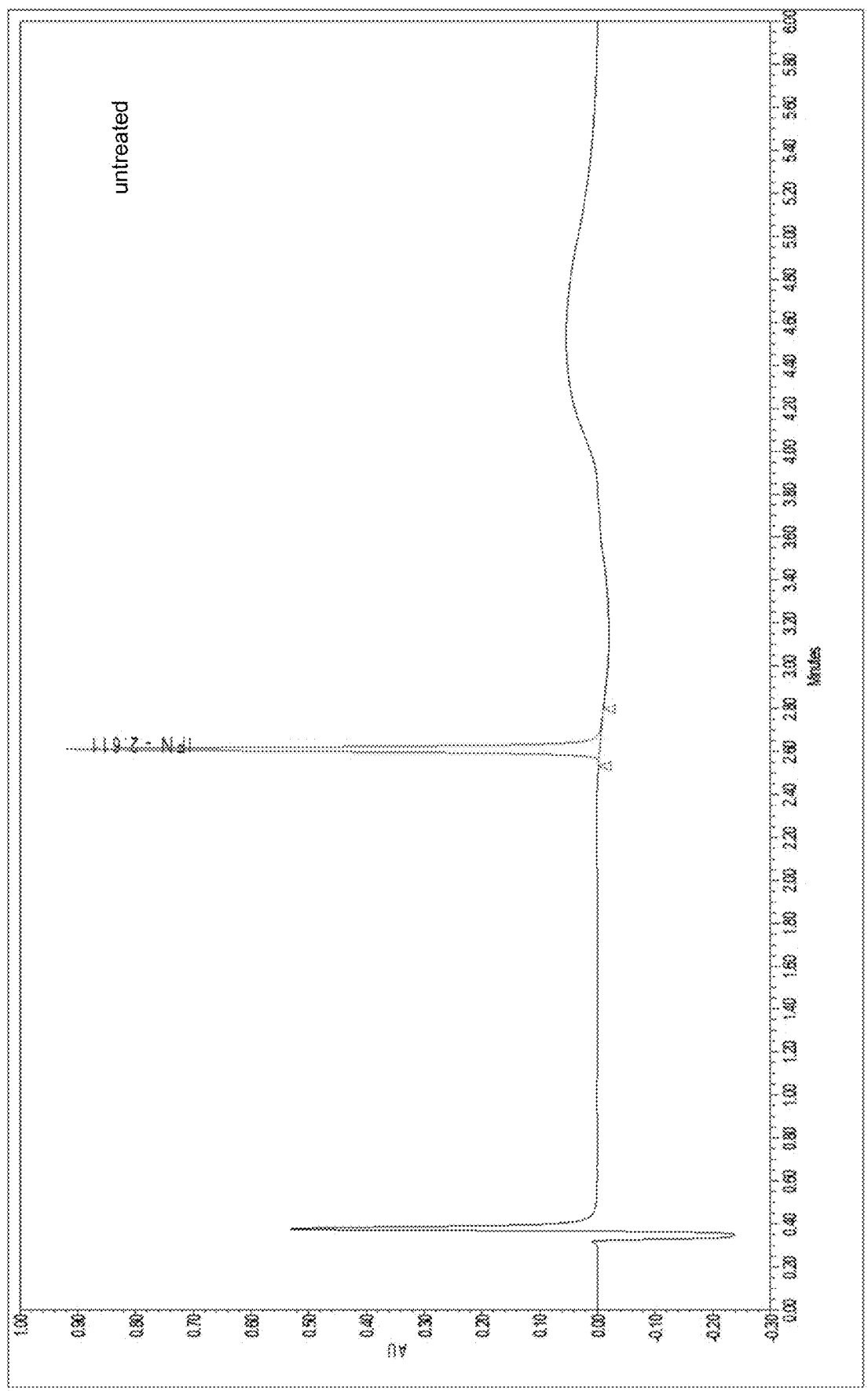
Figure 2A: RP-UPLC profiles of artificially degraded IFN-β-1a

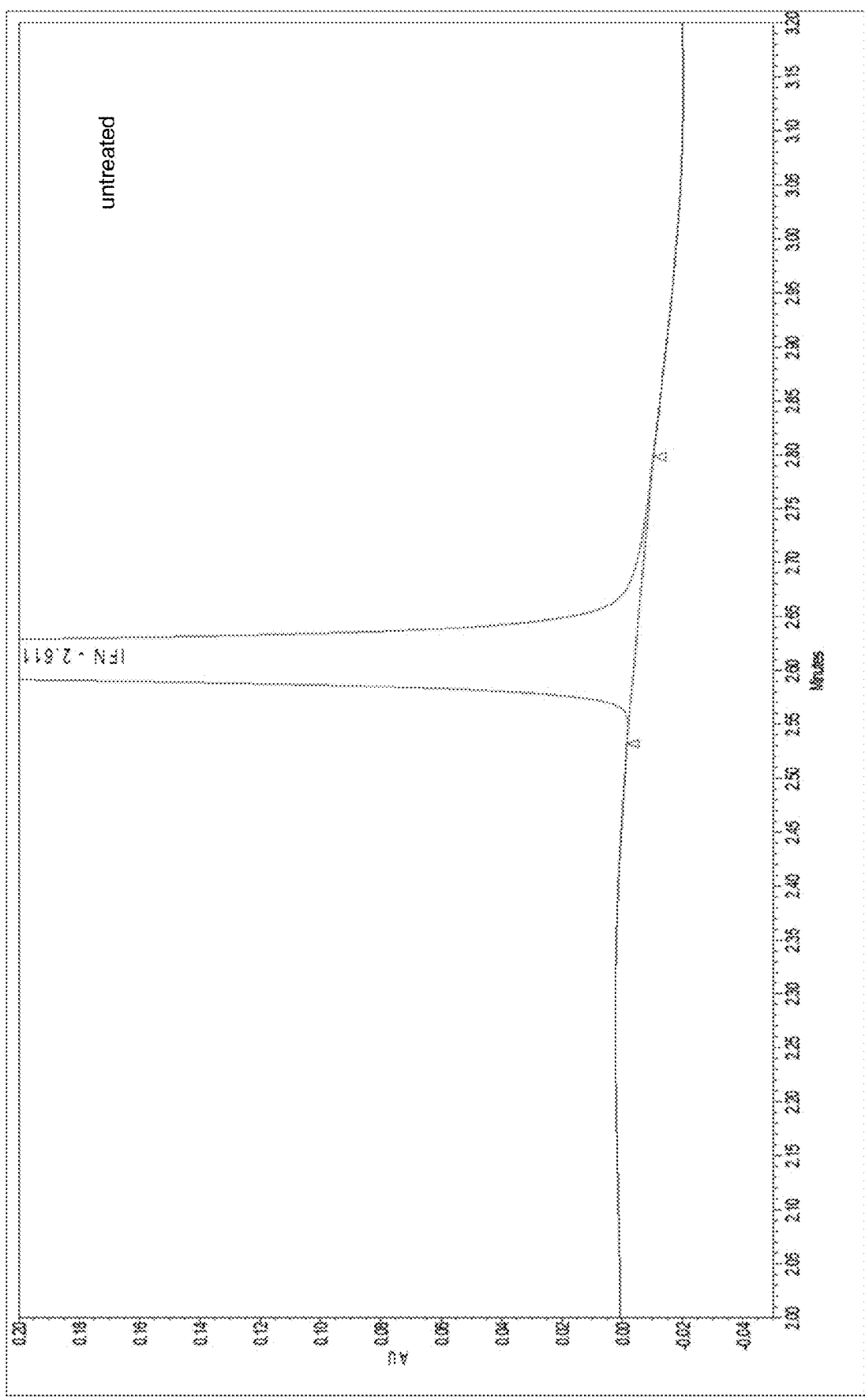
Figure 2B: RP-UPLC Untreated and Zoomed/de-desialylated/deamidated/de-sialylated-Deamidated

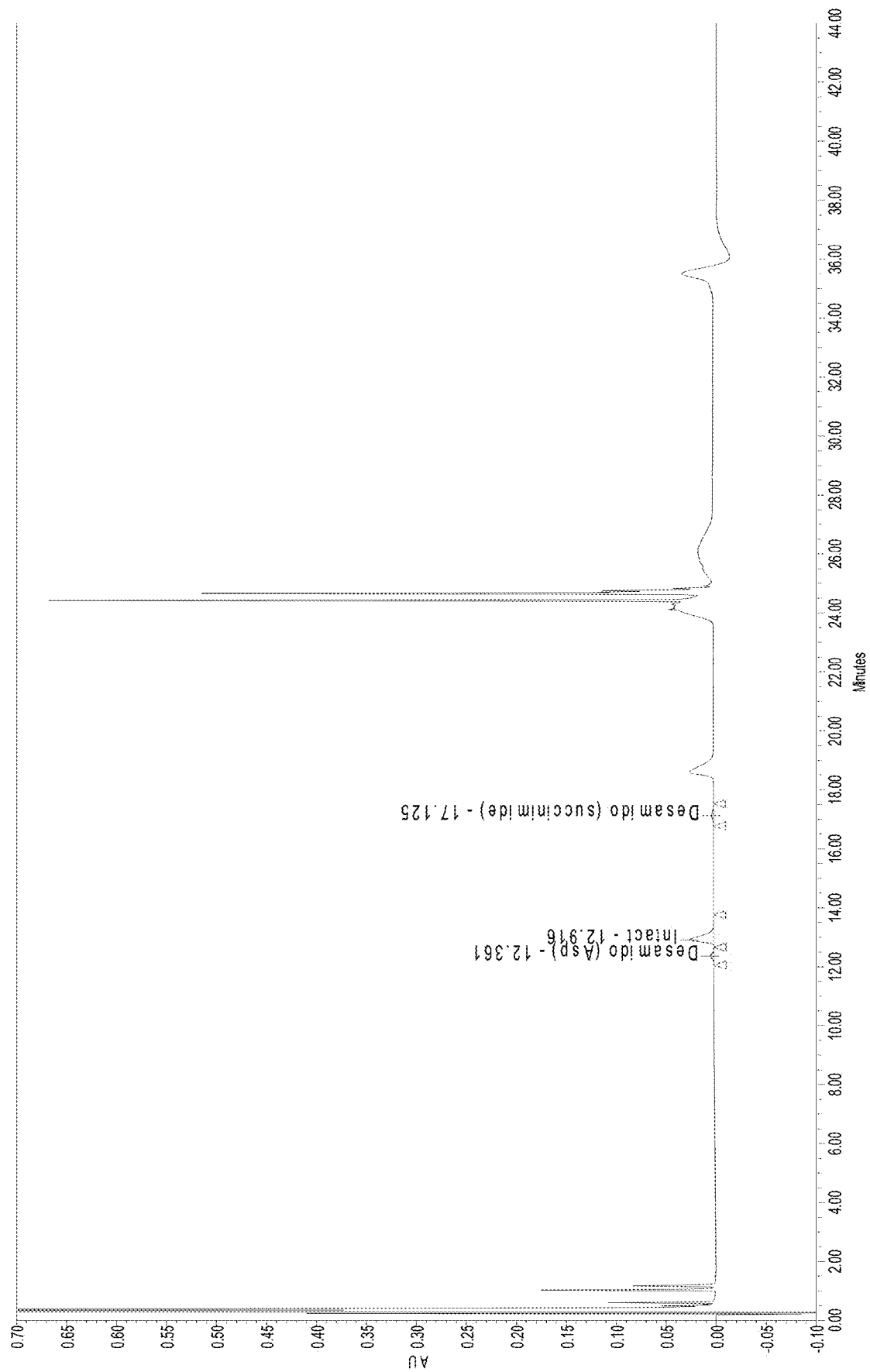
Figure 3A: Deamidation level of IFN-β-1a DS untreated

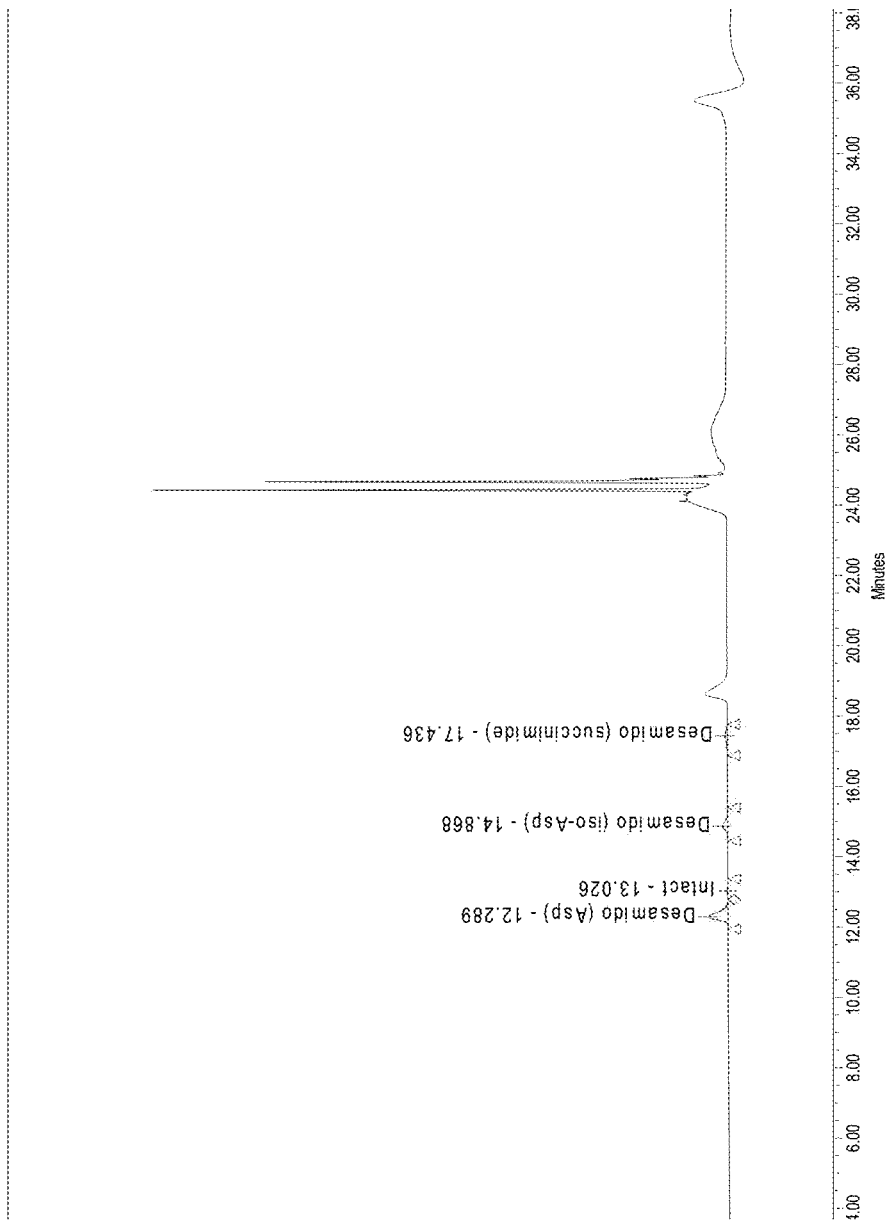
Figure 4A: Deamidation level of IFN-β-1a DS artificially deamidated

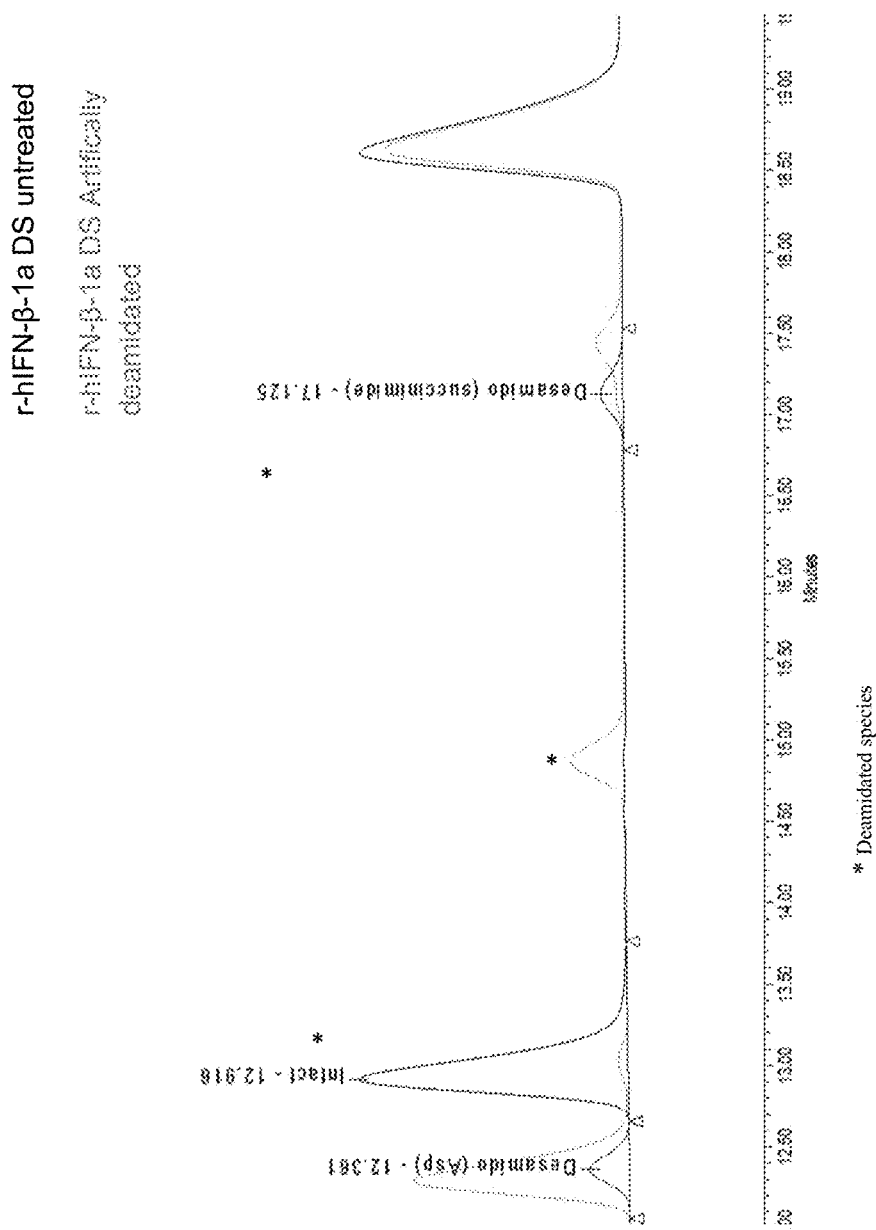
Figure 5: Overlay of IFN-β-1a DS untreated and artificially deamidated_zoom profile

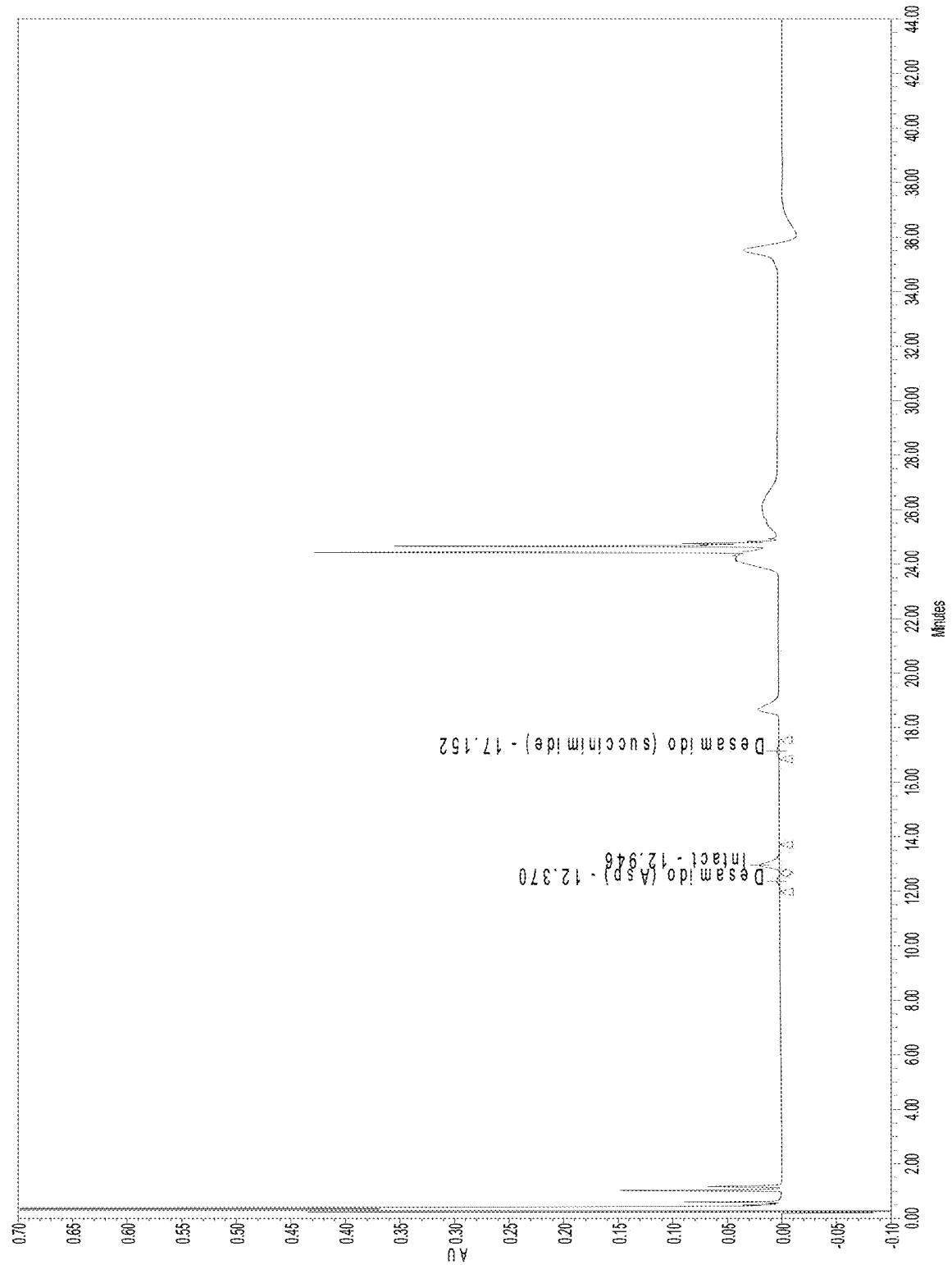
Figure 6A: Deamidation level of IFN-β-1a DS artificially de-sialylated

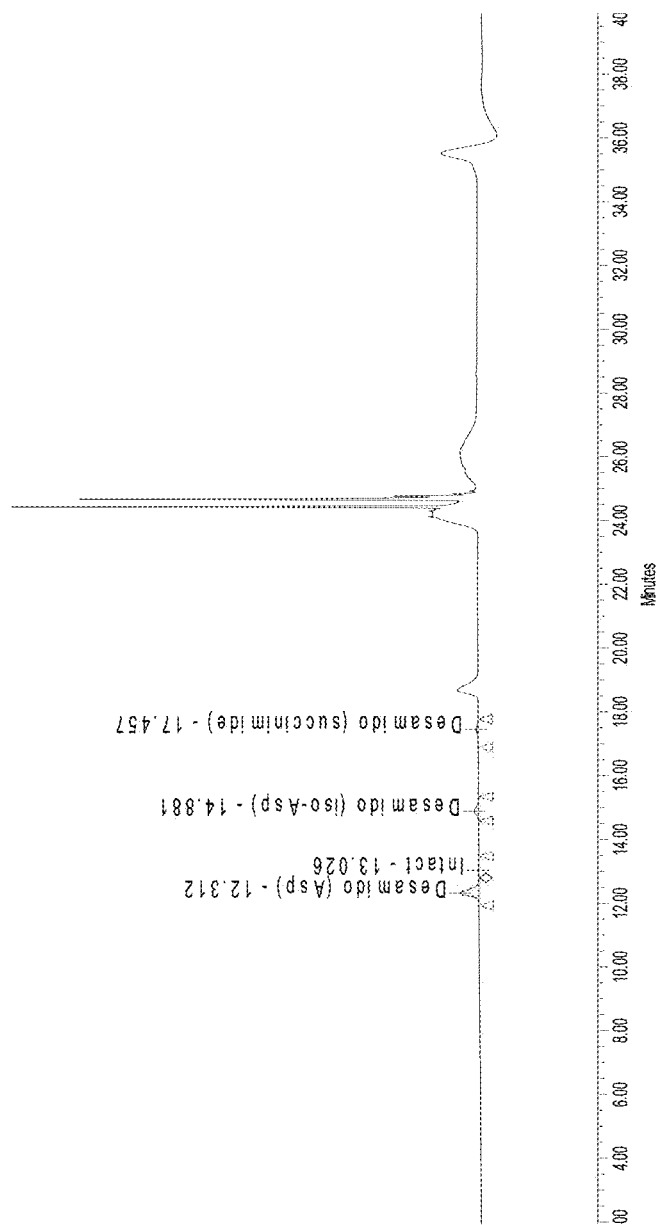
Figure 7A: Deamidation level of IFN-β-1a DS artificially deamidated and de-sialylated

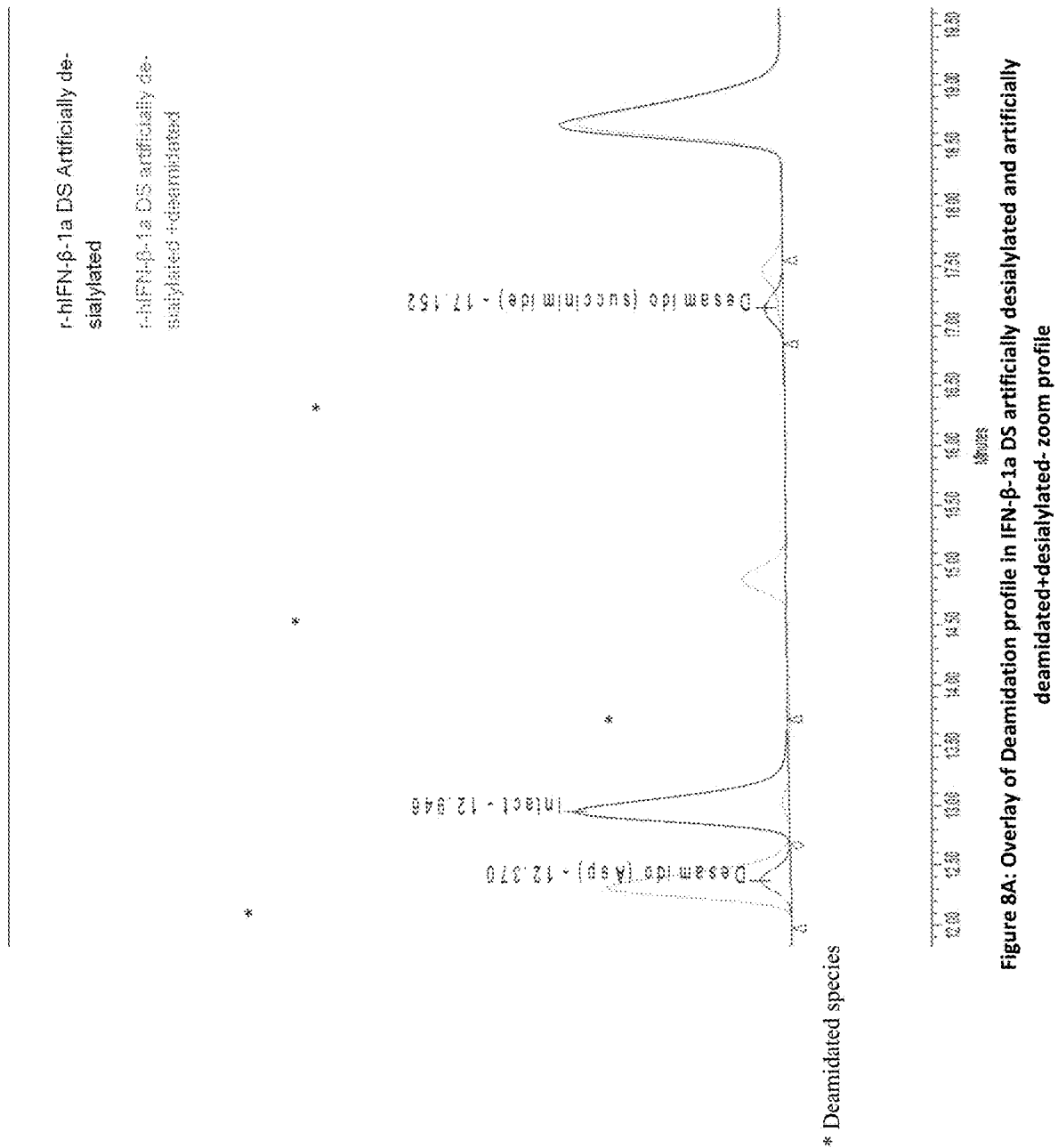
Figure 8A: Overlay of Deamidation profile in IFN-β-1a DS artificially desialylated and artificially deamidated+desialylated- zoom profile Figure 9: MHC class I immunomodulatory bioassay: dose response curves
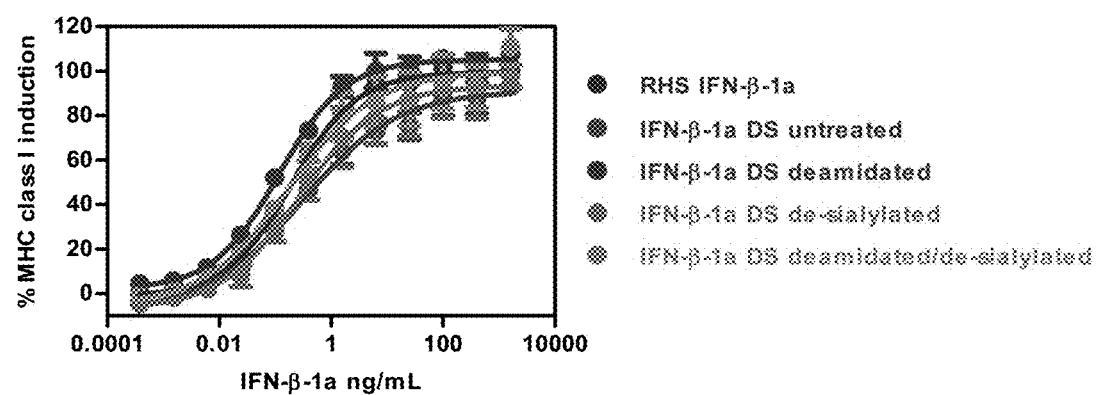

Figure 10: Immunomodulatory biological activity of IFN-ß-1a
| Sample | Potency | CV |
|---|---|---|
| IFN-β-1a DS untreated | 83% | 17% (n=3) |
| IFN-β-1a DS deamidated | 163% | 27% (n=4) |
| IFN-β-1a DS de-sialylated | 50% | 50% (n=3) |
| IFN-β-1a DS deamidated/de-sialylated | 97% | 19% (n=3) |
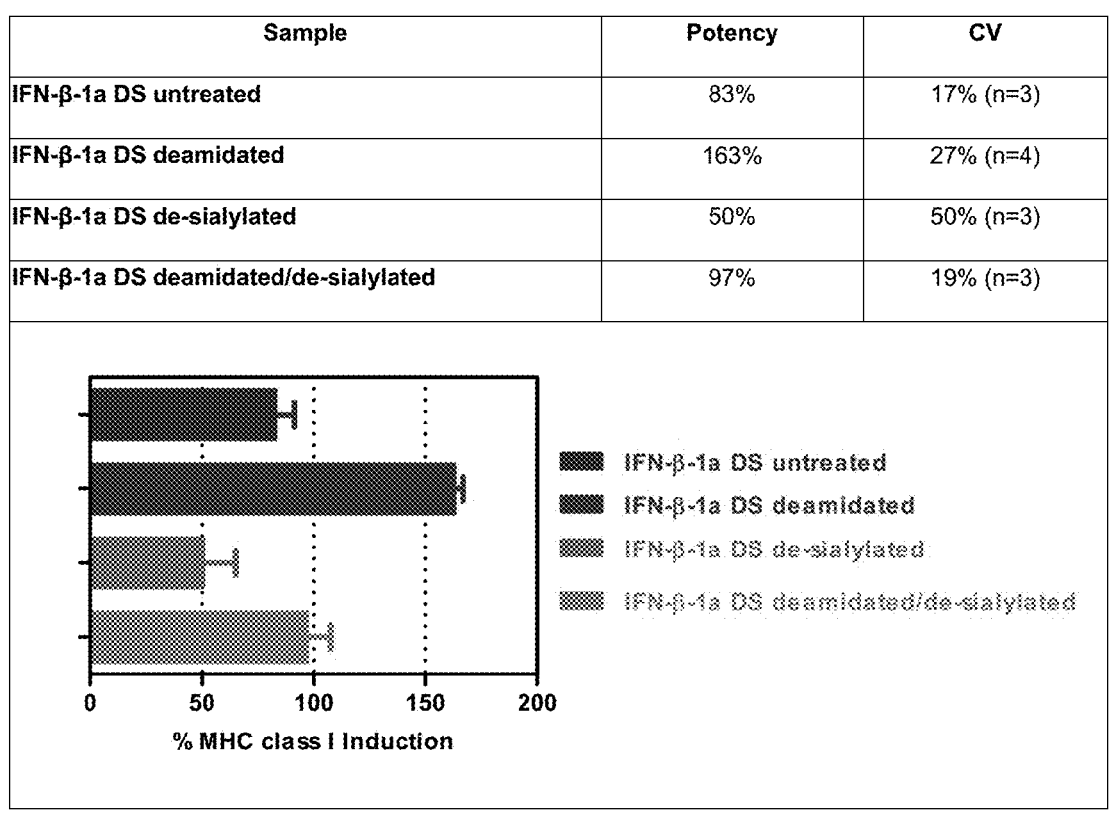

Figure 11: Antiviral activity by A549/EMCV system: dose response curves
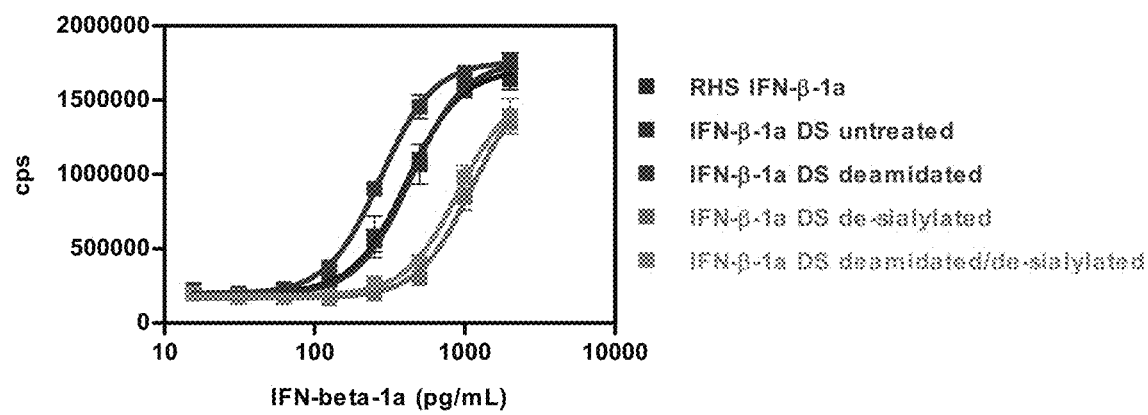

Figure 12: Antiviral activity of IFN-ß-1a
| Sample | Potency | CV |
|---|---|---|
| IFN-β-1a DS untreated | 91% | 1% (n=2) |
| IFN-β-1a DS deamidated | 140% | 10% (n=2) |
| IFN-β-1a DS de-sialylated | 37% | 20% (n=2) |
| IFN-β-1a DS deamidated/de-sialylated | 45% | 2% (n=2) |
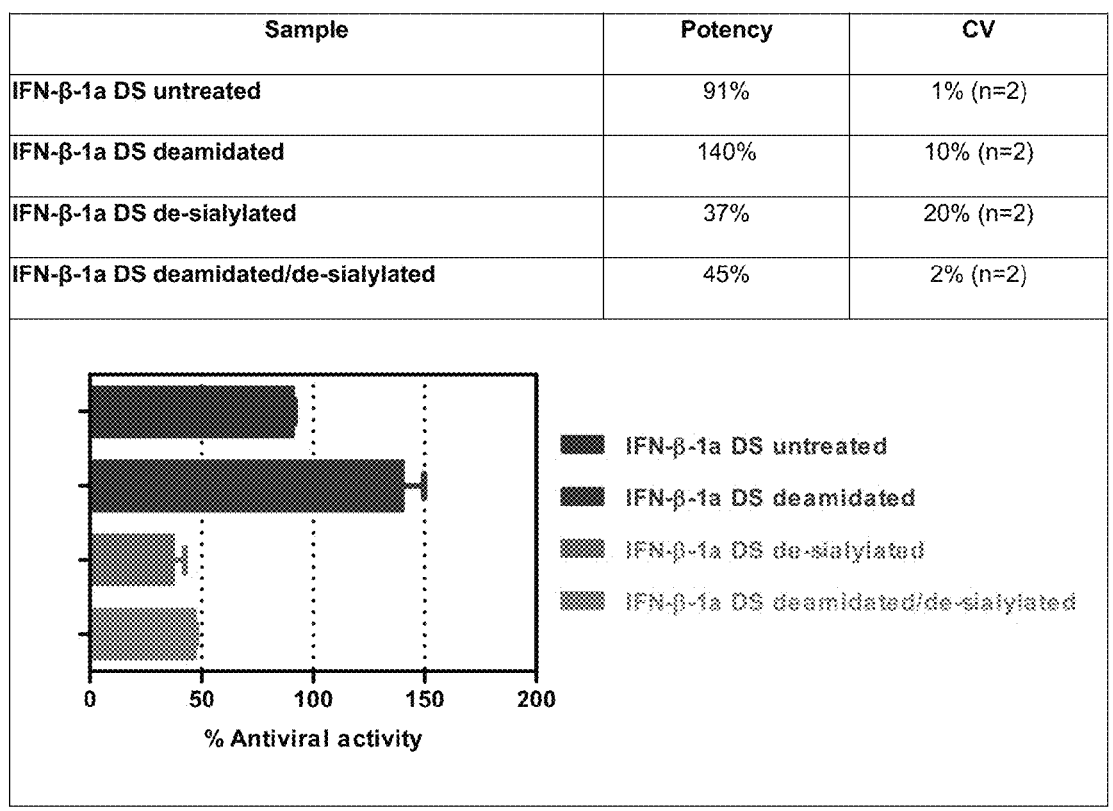

IFN BETA PROTEIN ANALOGS

CROSS-REFERENCE TO RELATED APPLICATIONS

This application is a divisional of U.S. Ser. No. 15/300,288, filed Sep. 29, 2016, which is the U.S. national stage application of International Patent Application No. PCT/EP2015/057205, filed Apr. 1, 2015.

The Sequence Listing for this application is labeled "Seq-List.txt" which was created on Aug. 20, 2018 and is 4 KB. The entire content of the sequence listing is incorporated herein by reference in its entirety.

DESCRIPTION

Background of the Invention

Natural interferon-beta (IFN-beta) is produced by cells mostly in response to viral infections or following an exposure to other biologicals. IFN-beta is implicated in antiviral, anti-proliferative and immuno-modulatory activities.

Several recombinant human interferon-beta preparations, referred to as Interferon-beta 1a and Interferon-beta 1b, are commercially available for the treatment of relapsing forms of Multiple Sclerosis (M Revel, Pharmacol Ther 2003 October, 100(1): 49-62). IFN-beta 1a is a 166 amino acid glycoprotein with a single N-linked carbohydrate chain on $Asn_{80}$ residue. The sequence comprises three cysteines of which two form a disulphide bond ($Cys_{31}$ and $Cys_{141}$) and one, $Cys_{17}$, is free and proximal to the surface, but buried. Interferon-beta 1b is non-glycosylated and has a Cys17Ser mutation.

Interferon-beta exerts its antiviral function in different ways; one is to elicit antiviral activity from the target cells (inhibition of viral replication) and the other is to induce apoptosis in infected cells (Taniguchi et al., Current Opinion in Immunology, February 2002, 14(1): 111-116). In addition to this direct action, interferon-beta affects cells of the immune system as well as it induces the expression of MHC-class I molecule on cell surface. The virus-infected cells can then be eliminated by cytotoxic T lymphocytes (CTL). This elimination mechanism is based on CTL recognition of viral antigens presented by MHC class I on surface of the infected cells.

Immuno-oncology is an evolving approach to cancer care focused on redirecting the patient's immune system to eliminate tumours.

One of the immuno mechanisms to clear tumour cells by the host system is the killing of tumour cells by CTL. This elimination mechanism is based on CTL recognition of tumour antigens presented by MHC class I on surface of the tumour cells.

Viruses and tumours can use immune evasion mechanisms which include the down modulation of MHC-class I expression.

Molecules which are able to increase the direct antiviral response and/or the elimination mechanism of infected cells by CTL as well as molecules having a direct anti-proliferative activity and/or the capacity to redirect the host immune system to kill tumour cells have the potential to act as a novel and more potent antiviral and cancer therapeutic agent.

WO 2006/053134 identifies an IFN-beta 1b protein that shows at most 40% deamidation by storage at 25° C. and 60% relative humidity for 6 months. This protein has an increased anti-viral and anti-proliferative activity. An increased immunomodulatory activity has not been reported.

Thus, there is still a need to provide a novel and more potent therapeutic IFN-beta analog, particularly an IFN-beta 1a analog.

The inventors of the present invention have surprisingly found that deamidation of IFN-beta 1a at an asparagine at amino acid position 25 leads to an increase in immunomodulation, e.g. upregulation of class I MHC and increased antiviral activity. In addition, the inventors unexpectedly found that the deamidation-induced increase in immunomodulatory and antiviral activity is dependent on sialylation of IFN-beta 1a.

Moreover, the inventors of the present invention found particular deamidation conditions that lead to an almost complete deamidation of IFN-beta 1a.

The deamidated IFN-beta protein of the invention may thus be produced with high biological efficiency and cost efficiency. Further, the modified IFN-beta protein of the invention may enhance clinical efficacy of, e.g., cancer immunotherapies and antiviral therapies, such as vaccines either alone or in combination with other therapeutic agents or means. In addition, IFN-beta therapies may profit from the use of lower doses of IFN-beta and a reduction of side effects related to IFN-beta treatment.

SUMMARY OF THE INVENTION

The invention provides a composition comprising interferon-beta (IFN-beta) protein, preferably IFN-beta 1a, at least 80% of which is deamidated at an amino acid asparagine located at an amino acid position corresponding to amino acid position 25 of an interferon-beta 1a protein according to SEQ ID NO:1.

The invention further provides a modified interferon-beta (IFN-beta) 1a protein wherein the amino acid asparagine at an amino acid position corresponding to amino acid position 25 of an interferon-beta 1a protein according to SEQ ID NO:1 is deamidated.

The invention further provides the composition or the modified IFN-beta 1a protein for use in therapy, for use as immunomodulating agent, for use as a vaccine or in cancer immunotherapy.

The modified IFN-beta 1a protein according to the invention has a sequence as defined by SEQ ID NO:2.

The invention further provides the composition or the modified IFN-beta 1a protein for use in the treatment of a condition selected from the group consisting of viral infections, cancer, and neuronal disorder.

The invention further provides a method of deamidating a protein, preferably IFN-beta, more preferably IFN-beta 1a, comprising:

(a) incubating the protein to be deamidated under alkaline conditions for about 16 to about 24 hours, preferably 20 hours; and (b) purifying the deamidated protein.

BRIEF DESCRIPTION OF THE FIGURES

The patent or application file contains at least one drawing executed in color. Copies of this patent or patent application publication, with color drawing(s), will be provided by the Office upon request and payment of the necessary fee.

FIGS. 1A and 1B show the primary structure (SEQ ID NO:1) and 3D model structure of human IFN-β-1a. IFN-β-1a is a 166 amino acid glycoprotein with a single N-linked carbohydrate chain on $Asn_{80}$ residue. The sequence comprises three cysteines of which two form a disulphide bond (Cys$_{31}$ and Cys$_{141}$) and one Cys$_{17}$ is free and proximal to the surface but buried.

FIG. 2A RP-UPLC Profiles or artificial degraded IFN-beta 1a.

FIG. 3A Deamidation Level of IFN-beta 1a untreated.

FIG. 4A Deamidation Level of IFN-beta 1a artificially deamidated.

FIG. 5 Deamidation Level of IFN-beta 1a untreated and artificially deamidated IFN-beta 1a in an Overlay.

FIG. 6A Deamidation Level of IFN-beta 1a artificially de-sialylated.

FIG. 7A Deamidation Level of IFN-beta 1a artificially deamidated and de-sialylated;

FIG. 9 MHC class I Immunomodulatory Bioassay: Dose Response Curves.

FIG. 10 Immunomodulatory Biological Activity of IFN-beta 1a.

FIG. 11 Antiviral Activity by A549/EMCV System: Dose Response Curves.

FIG. 12 Antiviral Activity of IFN-beta 1a.

DETAILED DESCRIPTION OF THE INVENTION

Figure 2A:
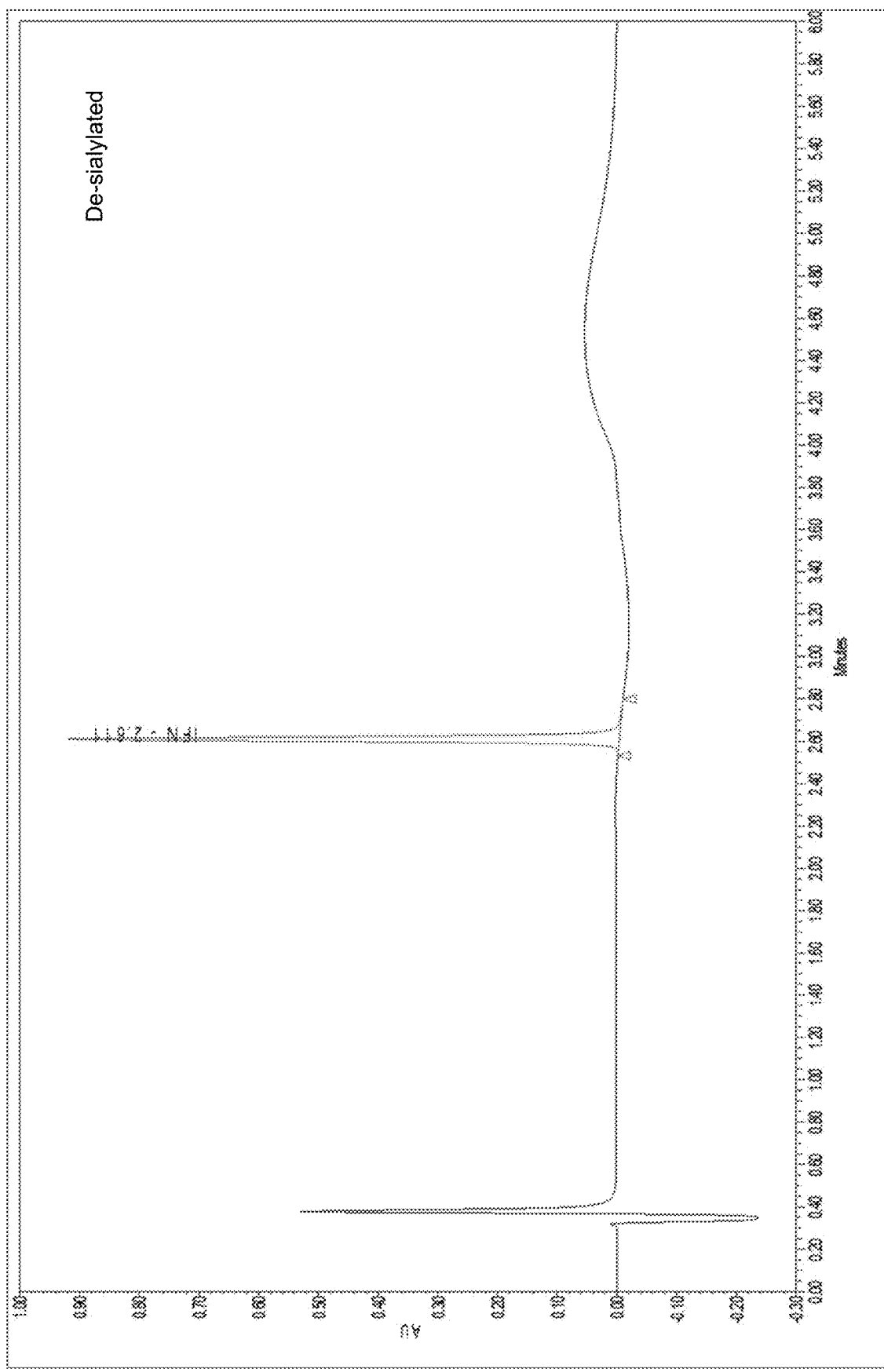

The present invention provides a composition comprising interferon-beta (IFN-beta), preferably IFN-beta 1a, protein at least 80% of which is deamidated at an amino acid asparagine located at an amino acid position corresponding to amino acid position 25 of an interferon-beta 1a protein according to SEQ ID NO:1 (see FIG. 1).

Further, the invention provides a modified IFN-beta 1a protein wherein the amino acid asparagine at an amino acid position corresponding to amino acid position 25 of an interferon-beta 1a protein according to SEQ ID NO:1 is deamidated.

The modified IFN-beta 1a protein according to the invention has a sequence as defined by SEQ ID NO:2.

Preferably, at least 85%, 90%, 95% or at least 96% of the IFN-beta protein, e.g. IFN-beta 1a, in the composition is deamidated, most preferably 96%.

Deamidation is one of the possible modification routes of proteins. This type of modification occurs mainly at asparagine and glutamine residues. For each asparagine undergoing deamidation, three possible modified products are formed:
  The succinimide intermediate (where the asparaginyl protein has lost a molecule of ammonia);
  The aspartyl protein (where the asparagine has undergone conversion into aspartic acid); and
  The isoaspartyl protein (where the asparagine undergone conversion into iso-aspartic acid; in this case the protein backbone continues on COOH of the side chain of the aspartic acid, instead of the COOH of the amino acid).

The last two modified products yield a change in the net charge of the protein, since the neutral amide side chain of the asparagine has been converted into the more acidic carboxyl group of aspartic acid.

Without being bound to any theory, it is expected that according to the spatial position of Asn25 (see FIG. 1B), its deamidation to Asp25 increases electrostatic interactions with a spatially close Arg147 with the possibility of forming additional hydrogen bonds with Arg147 and Thr144. The electrostatic interaction between aspartate and arginine can be spread over two oxygen atoms of the carboxylate and/or two nitrogen centres of the arginine guanidinium group as shown in FIG. 1B.

The composition as described herein comprises deamidated IFN-beta protein, e.g. IFN-beta 1a, in which the asparagine residue of the amino acid asparagine to be deamidated is replaced by an aspartate residue, an iso-aspartate residue or cyclic imidid residue such as succinimide. Preferably, about 65% to about 70%, more preferably about 68% of the asparagine residue is replaced by aspartate, about 15% to about 20%, more preferably about 18%, is replaced by isoaspartate and about 8% to about 13%, preferably about 11%, is replaced by succinimide.

Similarly, in the modified IFN-beta 1a protein as described herein, the asparagine residue of the amino acid asparagine to be deamidated is replaced by an aspartate residue, an iso-aspartate residue or cyclic imidid residue such as succinimide.

The compositions as described herein further exhibit an increased immunomodulatory activity, preferably an increased upregulation of class I MHC complexes compared to an IFN-beta protein, preferably of SEQ ID NO:1, produced in CHO cells. In particular, due to the increased upregulation of class I MHC, the deamidated or modified INF-beta proteins both as described herein may play a role in cancer immunotherapy or antiviral vaccination by restoring antigen presentation on cell surfaces of tumour or infected cells which in turn would result in increased number of targets on cell surfaces for CTL activity with a consequent increased efficacy in terms of cell killing activity by CTLs. This immunomodulatory activity might be exploited in IFN-beta monotherapies or in combination with conventional therapies, such as antiviral or cancer (immuno-)therapies.

The compositions as described further exhibit an increased antiviral activity (see Example 3.2).

Further, the modified IFN-beta 1a protein or composition both as described herein might comprise an IFN-beta protein that is glycosylated, particularly sialylated. The glycosylation might be an N-linked glycosylation attached to a nitrogen of asparagine or arginine residues; O-linked glycosylation attached to hydroxy oxygen of a serine, threonine, tyrosine, hydroxylysine or hydroxyproline residue; phospho-serine-linked glycosylation attached to serine residues; or C-linked glycosylation attached to a carbon on a tryptophan residue. Preferably, the glycosylation is an N-linked glycosylation. Most preferably, the glycosylation is attached to an asparagine corresponding to asparagine 80 of SEQ ID NO:1.

Further, the modified IFN-beta 1a protein or the composition both as described herein might comprise an IFN-beta protein that has the glycosylation pattern of an IFN-beta protein produced in any eukaryotic cell, such as Chinese hamster ovary (CHO) cells, human embryonic kidney cells (293T), human hepatocellular carcinoma cells (HepG2), human T cell leukemia cells (Jurkat), human T cell acute lymphoblastic leukemia cells (Molt4), human EBV-immortalized B-cell line (Dakiki), human rhabdomyosarcoma cells (RD) and human fibrosarcoma cells (HT1080), preferably CHO cells.

The glycan chains of the modified IFN-beta 1a protein might be a tri or tetra-antennary organization, preferably as performed in CHO cells.

Moreover, the modified IFN-beta 1a protein or the composition both as described herein might comprise an IFN-beta protein that is sialylated, preferably with N-acetylneuraminic acid, at the end of glycan chains attached to said modified IFN-beta 1a protein. Since the modification of the amino group of the sialic acid (e.g. by an acetyl or glycolyl group) and the amount of sialic acid per glycan antennae (e.g. tri- or tetra-sialylation) is tissue specific, sialylation of the glycan chains is preferably the sialylation as performed by CHO. In a particular preferred embodiment, all glycan side chains are sialylated, e.g. as performed by CHO cells.

The composition of the invention might comprise as active agent an IFN-beta protein alone or an IFN-beta protein in combination with other therapeutic agents as described herein, optionally together with a pharmaceutically acceptable carrier, adjuvant or additive as described herein, e.g. as an aqueous solution optionally with further carriers, adjuvants or additives as described herein.

Similarly, the modified IFN-beta 1a protein as described herein might be used alone or in combination with other therapeutic agents or pharmaceutically acceptable carriers both as described herein.

The composition as described herein might comprise a pharmaceutically acceptable carrier, adjuvant or additive. Such carriers, adjuvants or additives are known in the art and depend on the indication and localization of application in the body. The choice of them might also consider the releasing rate of the therapeutic agent, e.g. immediate release or retard. The compositions or modified IFN-beta 1a protein both as described herein are preferably for systemic administration. The composition or modified IFN-beta 1a protein might be administered orally, locally, e.g., on the skin, or parenterally, preferably via injection of infusion.

Carriers, adjuvants or additives for parenteral administration are aqua sterilisata, reagents influencing the pH, such as organic and anorganic acids and salts thereof, buffers for adjusting the pH, isotonicity agents, such as natrium chloride, natrium hydrogen carbonate, glucose, fructose, detergents and emulgators, such as TWEEN, CREMOPHOR, oils, such as peanut oil, *soja* bean oil, *ricinus* oil, synthetic fatty acid ester, polymeric carriers, complexing agents, preservatives and stabilizers.

The composition as described herein might further comprise an anti-oxidant, such as natrium sulfit or methionine, preferably methionine.

Similarly, the modified IFN-beta 1a protein as described herein might be in combination with an anti-oxidant as described herein.

In a further embodiment of the invention, the composition or modified IFN-beta 1a protein both as described herein is for use in therapy, as an immunomodulating agent, as a vaccine or in cancer immunotherapy.

The composition or modified IFN-beta 1a protein both as described herein might be either alone or in combination with other therapeutic agents, such as antiviral agents, e.g. ribavirin, vaccines, immunomodulators such as tumor immunotherapeutics, cytokines, interleukins or chemokines (L-BLP-25 or other tumour-associated antigens).

An immunomodulating therapy might be designed to elicit or amplify an immune response. Alternatively, the immunomodulating therapy might reduce or suppress the immune response. In a preferred embodiment of the invention, the immunomodulating therapy elicits or amplifies the immune response. The inventive composition or modified IFN-beta 1a protein both as described herein as an immunomodulating agent might be used alone or in combination with other immunomodulators as described herein.

The vaccine as described herein might be a prophylactic, a therapeutic vaccine or a cancer vaccine. The vaccine might further comprise pharmaceutically acceptable carriers for injection, nano-patch or oral delivery of the vaccine. Such carriers are known by those skilled in the art and might comprise adjuvants, such as albumin, preservatives, such as benzyl alcohol, phenol, m-cresol, formaldehyde or thimerosal, antibiotics and/or stabilizers, such as MSG or 2 phenoxyethanol.

The composition or modified IFN-beta 1a protein both as described herein might be used in the treatment of a condition selected from the group consisting of viral infections, cancer, and neuronal disorder in a subject.

The composition or modified IFN-beta 1a protein both as described herein might be used in the treatment of viral infections caused e.g. by hepatitis C virus (HCV), Influenza, Dengue, etc. In particular, HCV might cause hepatitis C or chronic liver-related diseases such as cirrhosis, liver failure, and hepatocellular carcinoma which are also treated by the inventive composition or modified IFN-beta 1a protein, both as described herein.

Cancers that might be treated by the composition or modified IFN-beta 1a protein both as described herein might be selected from the group consisting of breast cancer, lung cancer, such as non-small cell lung cancer, liver cancer, colorectal cancer, prostate cancer, ovary cancer, brain cancer, biliary cancer, pancreatic cancer, etc.

The composition or modified IFN-beta 1a protein both as described herein might also be used for the treatment of neuronal disorders, such as nerve trauma. For example, they may be used for nerve regeneration, such as regeneration of the visual nerve, e.g. wherein said treatment comprises regulation of synaptic plasticity or enhancement of axonal.

The composition or modified IFN-beta 1a protein both as described herein might also be used for the treatment of neuronal disorders, such as multiple sclerosis.

A preferred subject as described herein might be a dialysis patient with an HCV infection.

The treatments as described herein might comprise immunomodulation, preferably upregulation of class I MHC complexes as described herein.

The composition and modified IFN-beta 1a protein both as described herein might further be used as described herein in combination with chemoimmunotherapy, chemotherapy, radiotherapy, a vaccine and/or a further therapeutic agent, such as an antiviral agent such as ribavirin, a cytokine such as IL-2 or IFN-alpha or a chemotherapeutic antibody such as rituximab.

For example, the inventive composition or modified IFN-beta 1a protein both as described herein might be used in combination with chemoimmunotherapy, such immunotherapies being based on tumor-associated antigens, for example in combination with L-BLP25.

The inventive or modified IFN-beta 1a protein both as described herein might be used as described herein in combination with chemotherapy and/or radiotherapy. In particular, the modified protein or composition might be used to enhance antitumor immune response through T cell cytotoxicity during metronomic chemotherapy, as well as to increase efficacy of combined chemo- (or radio-)therapy.

The invention further provides a method of deamidating a protein, comprising:
(a) incubating the protein to be deamidated under alkaline conditions for about 16 to about 24 hours, preferably 20 hours; and
(b) purifying the deamidated protein.

Preferably, the protein to be deamidated is IFN-beta, particularly IFN-beta 1a.

The incubation as described herein might be conducted at a pH of about 8.9 to about 9.5, preferably at about pH 9.2.

Moreover, the incubation as described herein might be conducted in any suitable buffer for deamidation. Such buffers are known by those skilled in the art. Preferably, the incubation is conducted in ammonium hydrogen carbonate, more preferably at a final concentration of 0.2 M.

Further, the incubation as described herein is at a temperature of about 20° C. to about 25° C., such as about 21° C. to about 24° C., preferably at about 23° C.

The purification as described herein may comprise any purification methods known in the art. Preferably, the purification comprises ultra-filtration, more preferably ultra-filtration with ammonium acetate pH 3.8.

Examples

1. Preparation of Deamidated IFN-Beta

Different IFN-β-1a degraded forms were prepared by chemical (basic pH for deamidated) and enzymatic (sialidase for de-sialylated) treatment of IFN-β-1a DS (drug substance) material.

The experimental design foresaw physic-chemical and biological characterization of untreated and artificially deamidated IFN-β-1a aimed at evaluating the impact of deamidation on IFN-β-1a immunomodulatory and antiviral activity. Moreover the design included the testing of the untreated and deamidated samples after sialic acid removal as well in order to evaluate the role, if any, of sialylation in regulating these specific biological activities.

Artificially degraded samples have been prepared as described hereafter:
  Deamidation was carried out by incubating the IFN-beta-1a DS into 1.2M Ammonium Bicarbonate pH 9.2, at 23° C. for 20 h. Final Ammonium Bicarbonate concentration prior to the incubation is about 0.2M and IFN-beta-1a concentration is about 0.3 mg/mL. Alkaline conditions are generally used to induce conversion of asparagine into aspartic acid and have been proven in the past to efficiently and consistently deamidate IFN-β-1a.
  Deslalylation was carried out by incubating the protein with Sialidase from Glyko (ref. GK80040) at pH 6.0, 37° C. for 1 h. This enzyme is capable of specifically releasing sialic acid attached to glycan structures. This treatment was applied to native as well as artificially deamidated IFN-β-1a.

After each treatment, samples have been ultra-filtered in order to exchange their buffers with 50 mM Ammonium Acetate pH 3.8 (IFN-beta-1a DS buffer) to have a matrix comparable to the untreated DS. Each IFN-β-1a degraded sample was then tested to confirm the success of the treatment, the extent of the specific degradation and its impact on biological activity.

2. Results on Physio-Chemical Characterization 2.1 Assay by RP-UPLC—Results

Figure 2A:
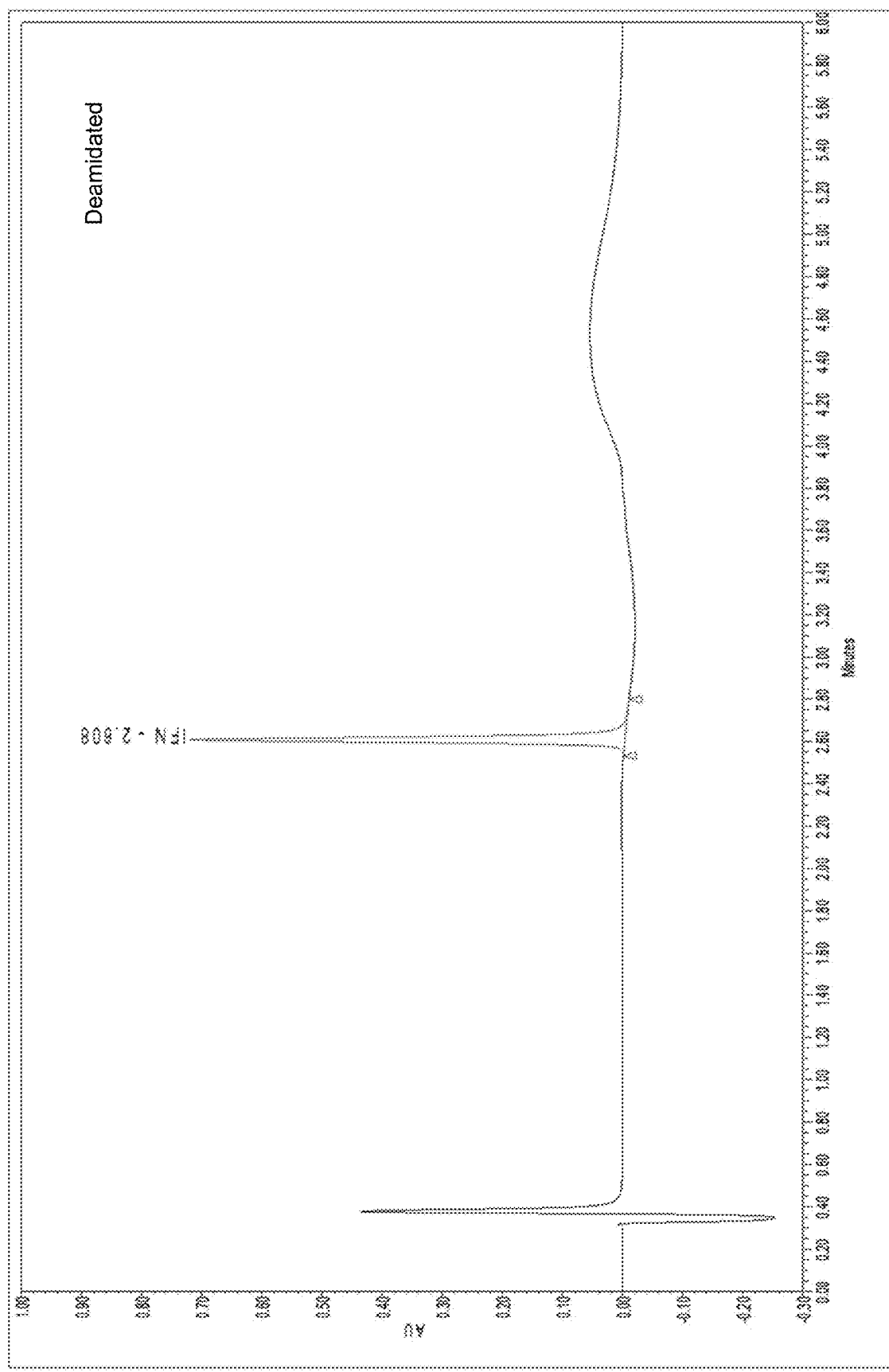
Figure 2A:
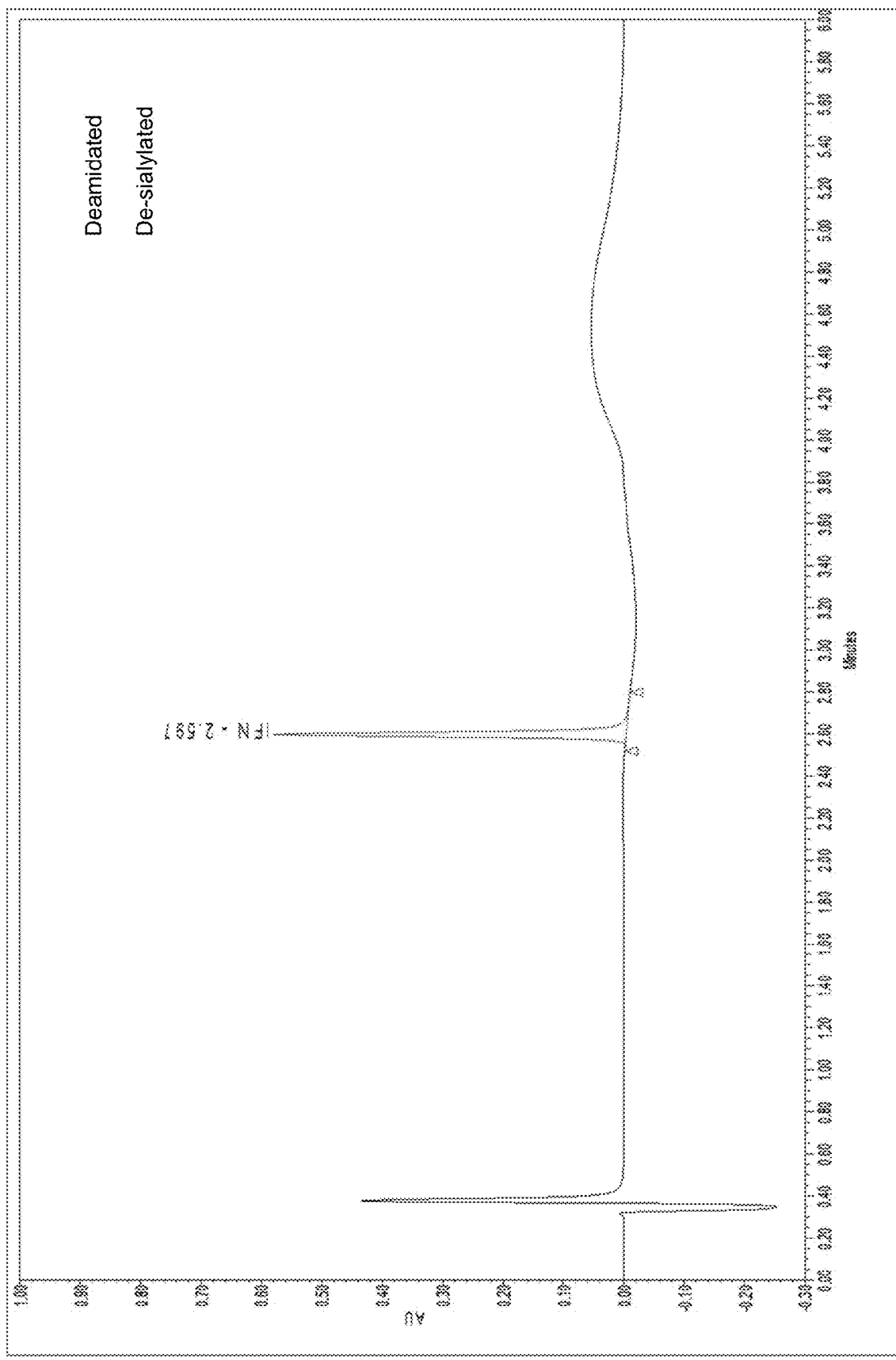
Figure 2B:
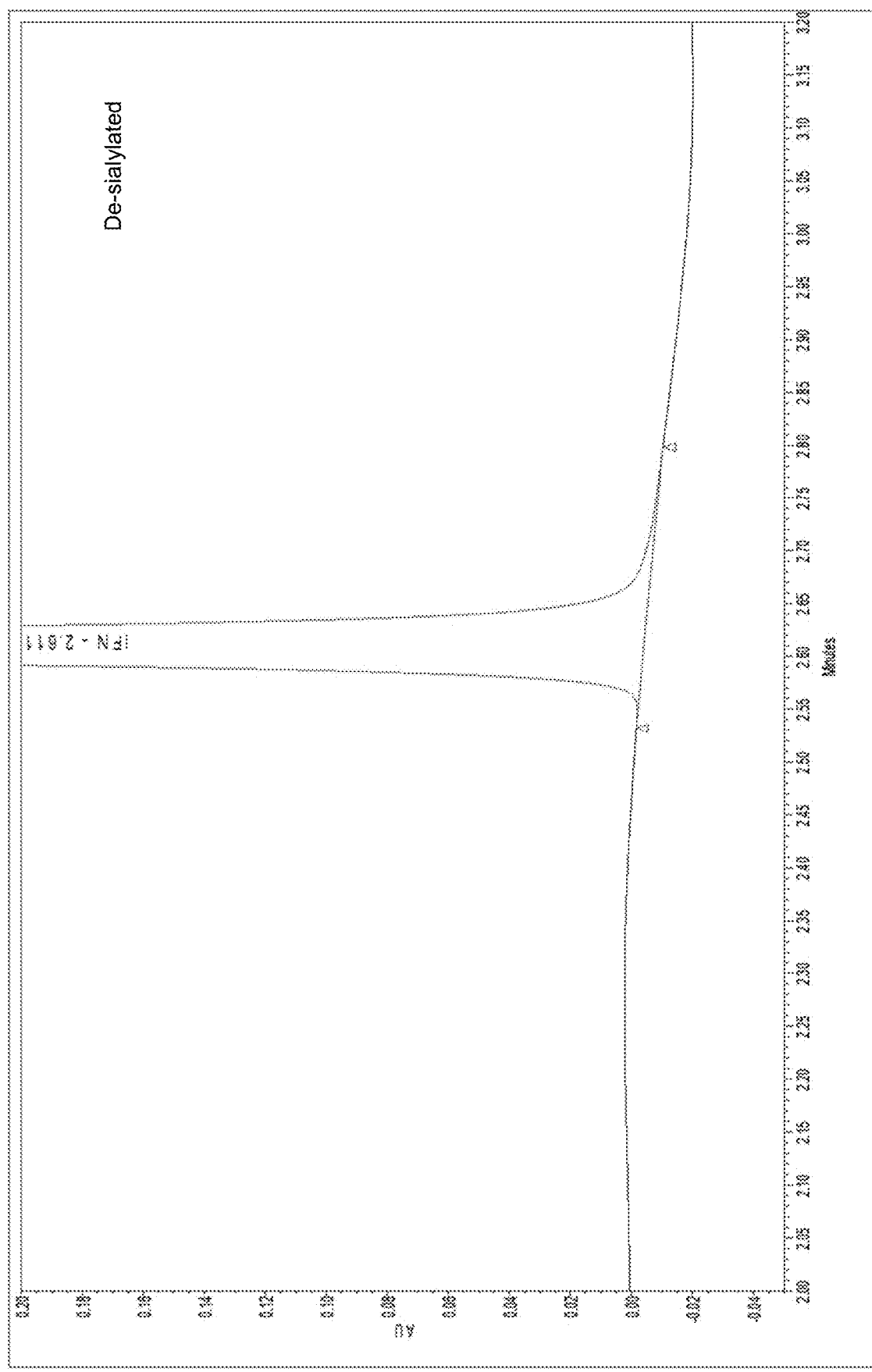
FIG. 2B is a partial enlargement of FIG. 2A.
Figure 2B:
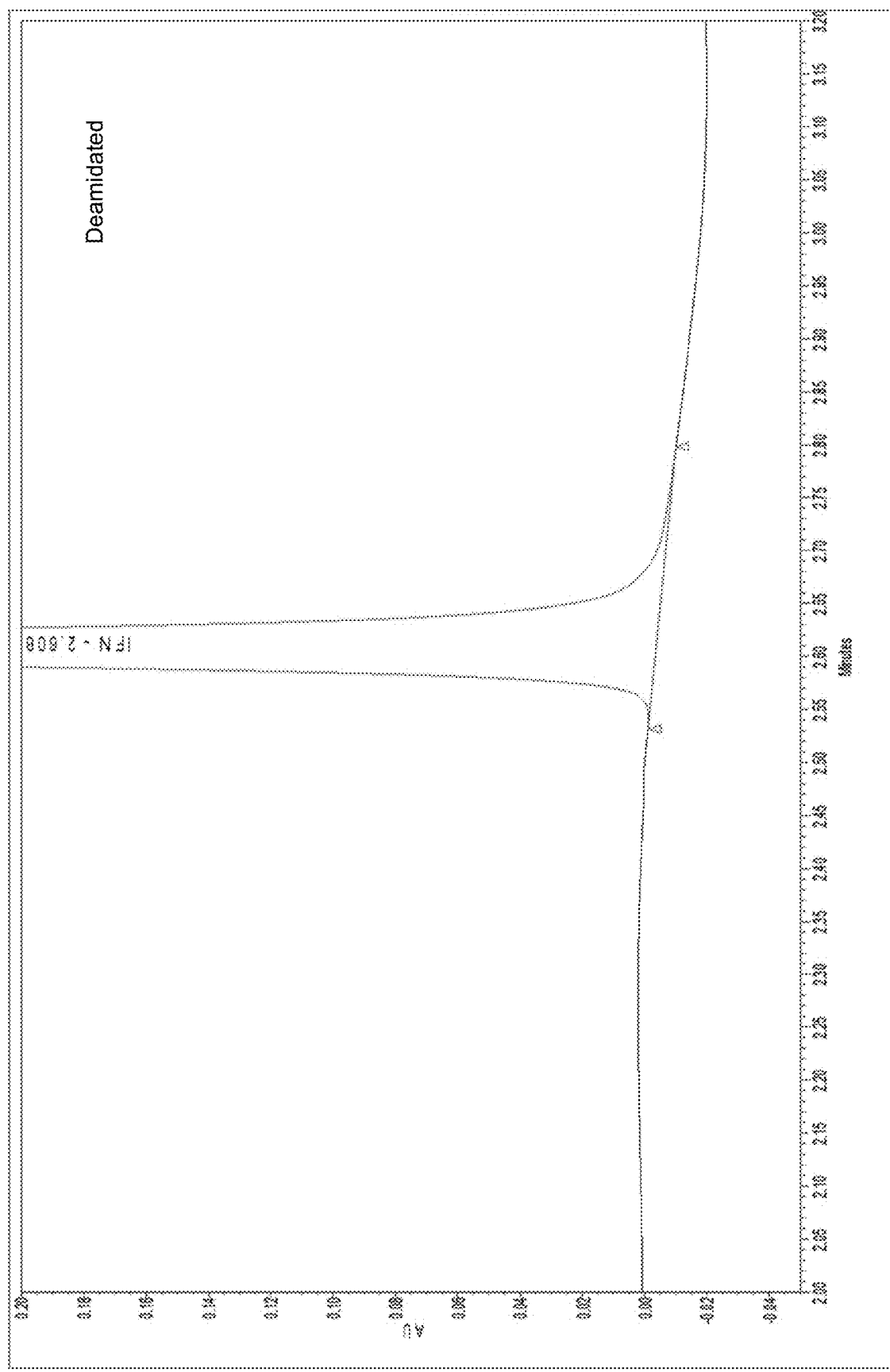
Figure 2B:
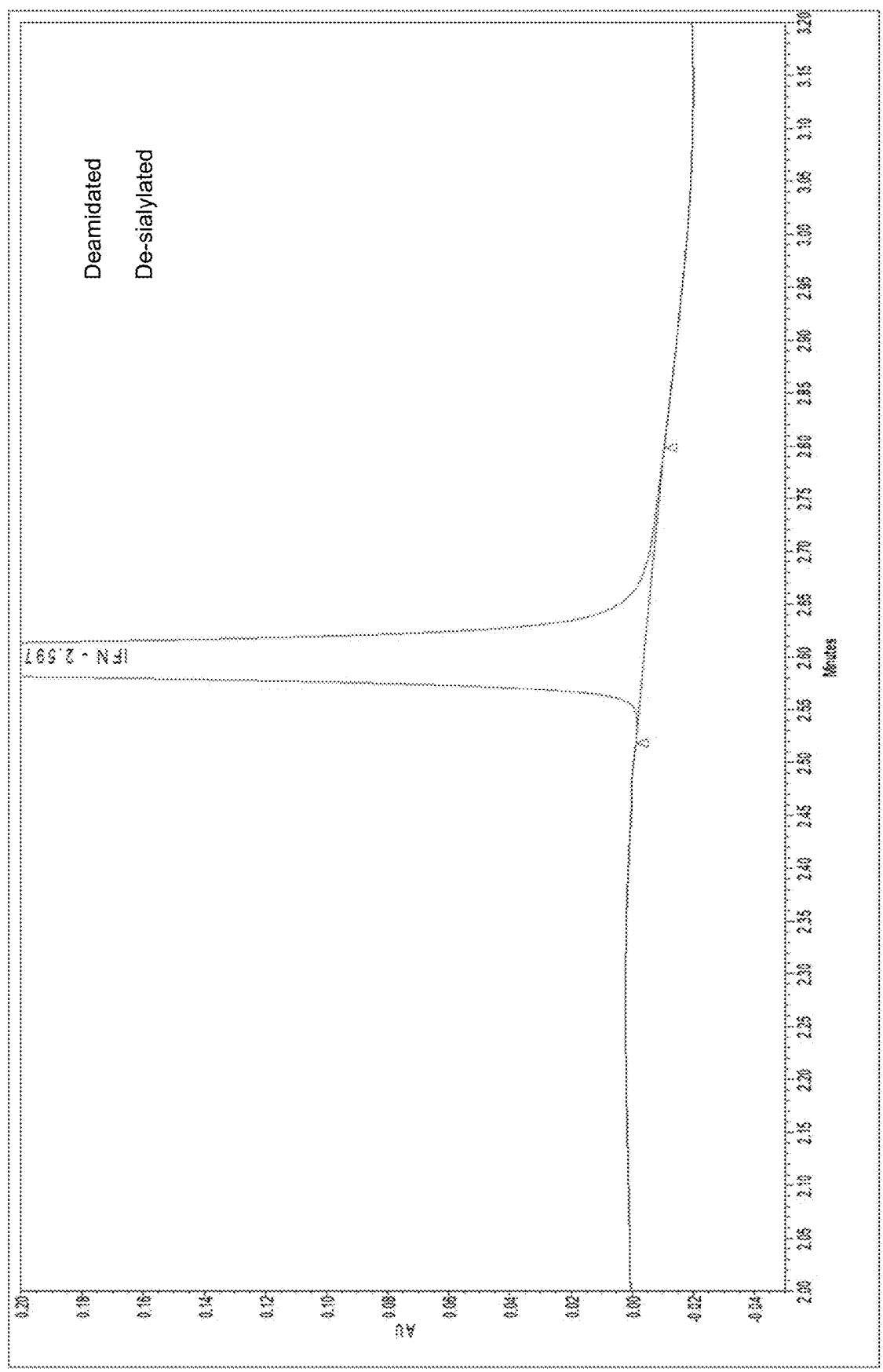

In FIG. 2, the results obtained in terms of UV profiles and protein concentration for all samples prepared is summarised. All profiles in FIG. 2 show a sharp peak of IFN-β-1a, demonstrating an optimal chromatographic performance for the untreated IFN-β-1a as well as for all artificially degraded samples.

TABLE 1

| Protein content by RP-UPLC | |
|---|---|
| Sample | IFN-B-1A Content µg/mL |
| IFN-β-1a DS artificially Deamidated | 898 |
| IFN-β-1a DS artificially Deamidated and Desialylated | 691 |
| IFN-β-1a DS artificially Desialylated | 300 |
| IFN-β-1a DS untreated | 382 |

Data reported above have been employed as a reference content within the study.

Sample corresponding to untreated IFN-beta 1a shows protein content aligned to the value expected for an untreated IFN-beta 1a (~300 µg/ml). Protein content detected both in IFN-beta 1a artificially deamidated and IFN-beta 1a artificially deamidated and desialylated is higher than the untreated IFN-beta 1a because of sample ultrafiltration and concentration in Amicon Ultra.

All samples have shown an IFN-β-1a concentration and amount suitable for carrying out all planned characterization tests.

2.2 Deamidation Level by Peptide Mapping/UPLC—Results

Figure 3B:
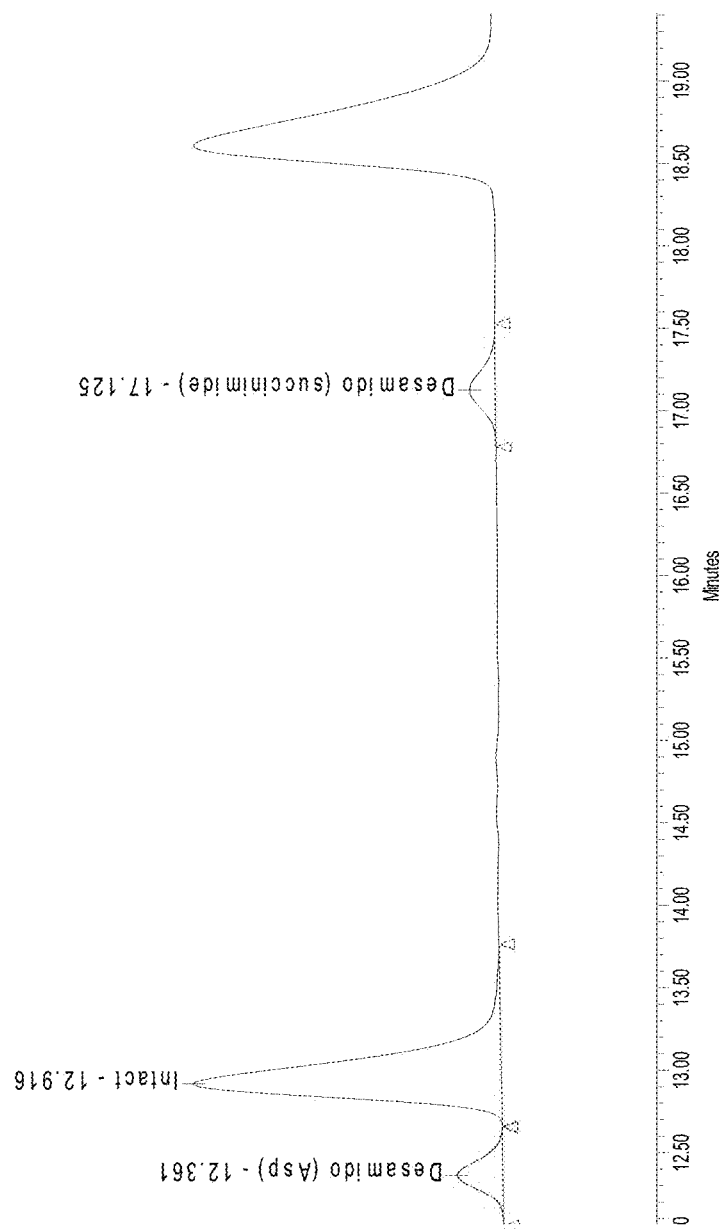
FIG. 3B is a partial image enlargement of FIG. 3A.
Figure 4B:
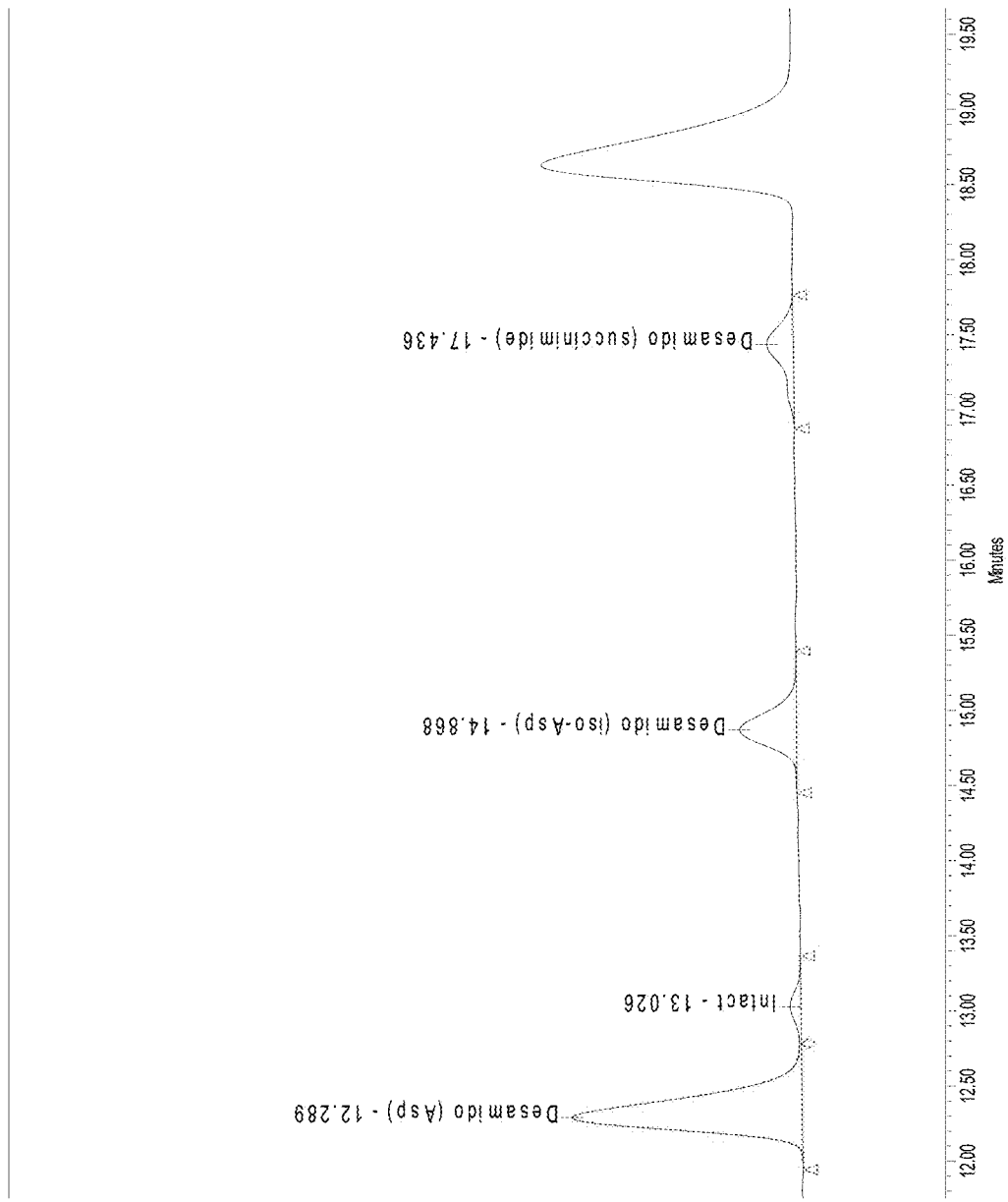
FIG. 4B is a partial image enlargement of FIG. 4A.
Figure 6B:
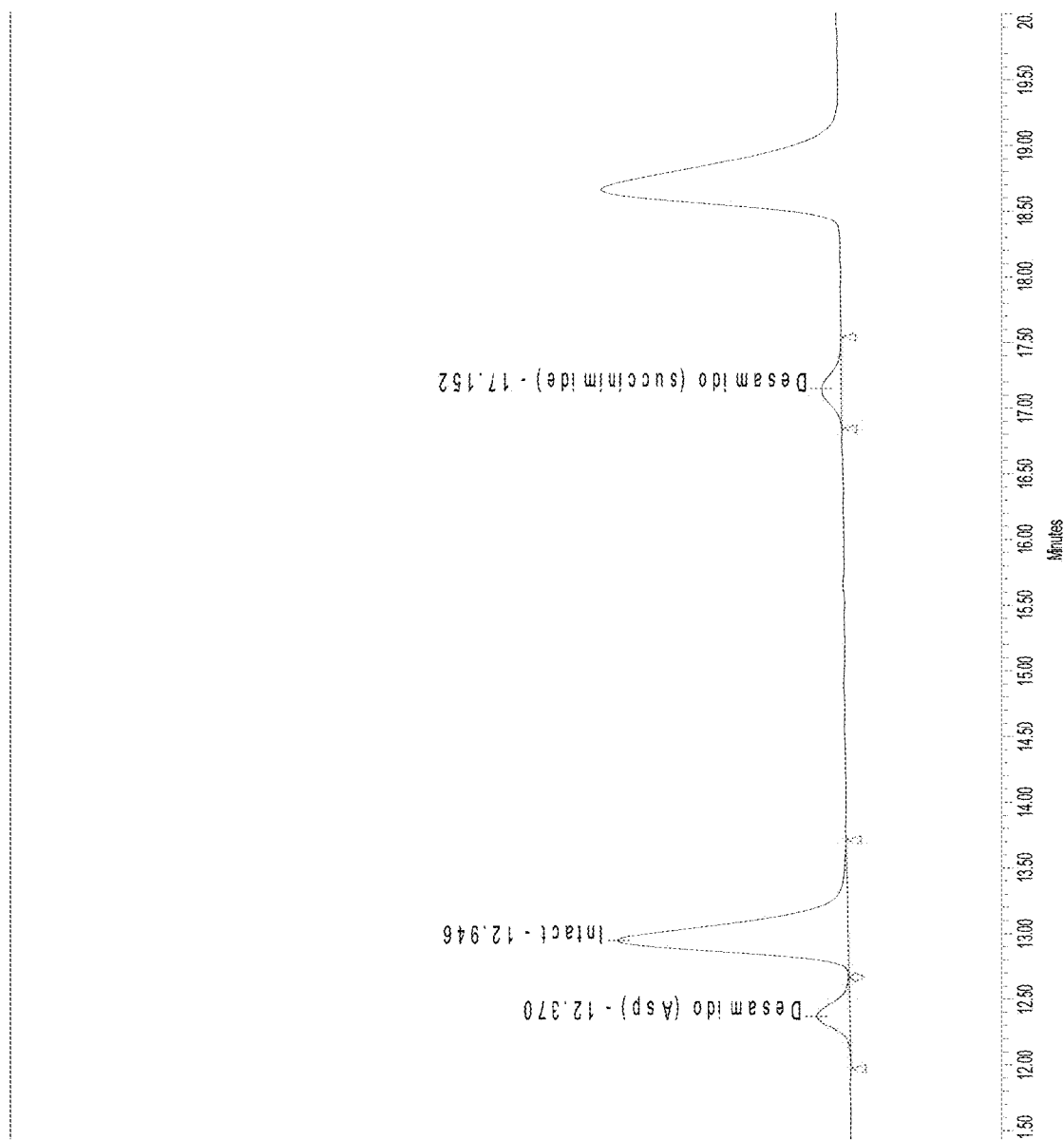
FIG. 6B is a partial image enlargement of FIG. 6A.
Figure 7B:
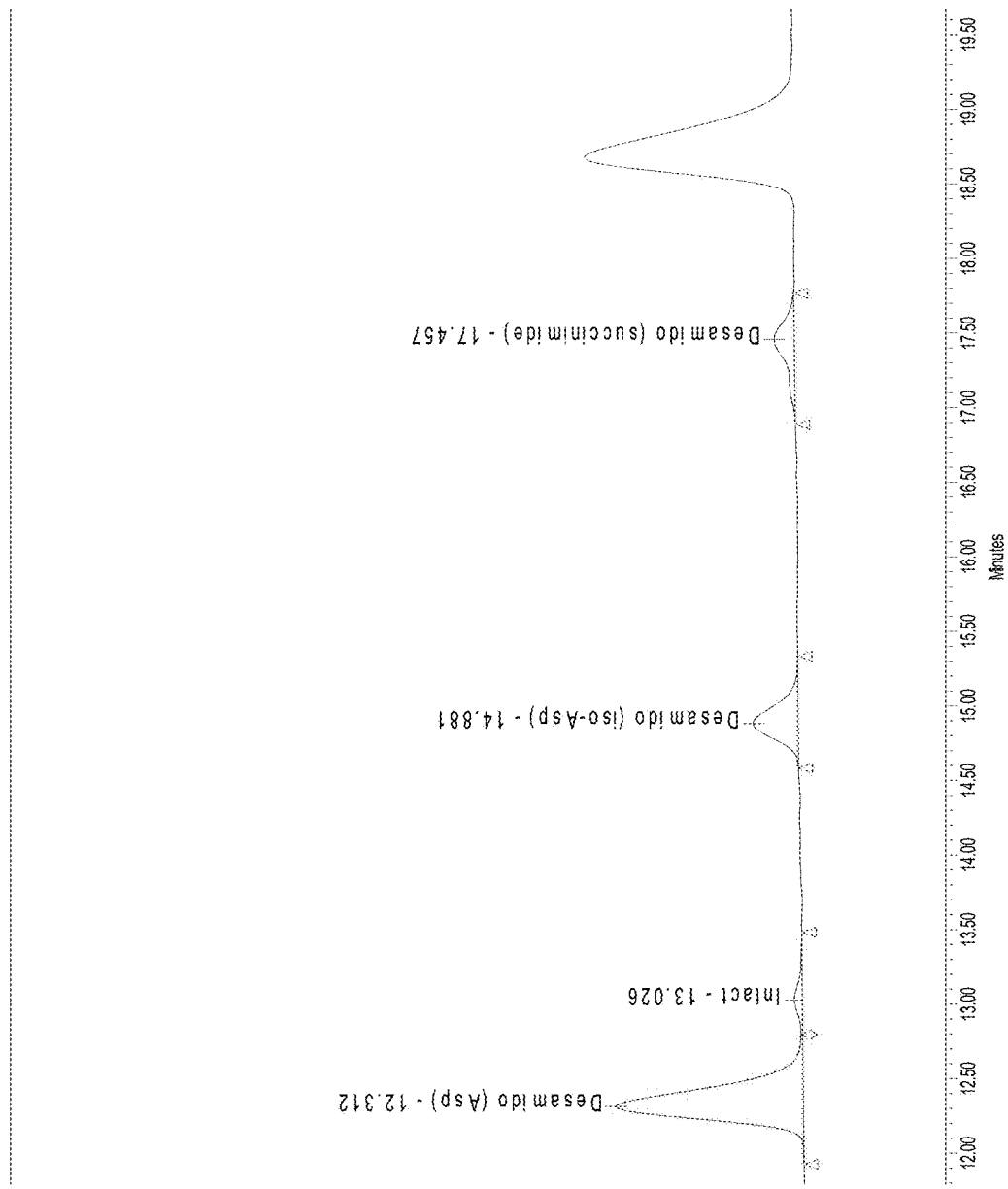
FIG. 7B is a partial image enlargement of FIG. 7A.
Figure 8B:
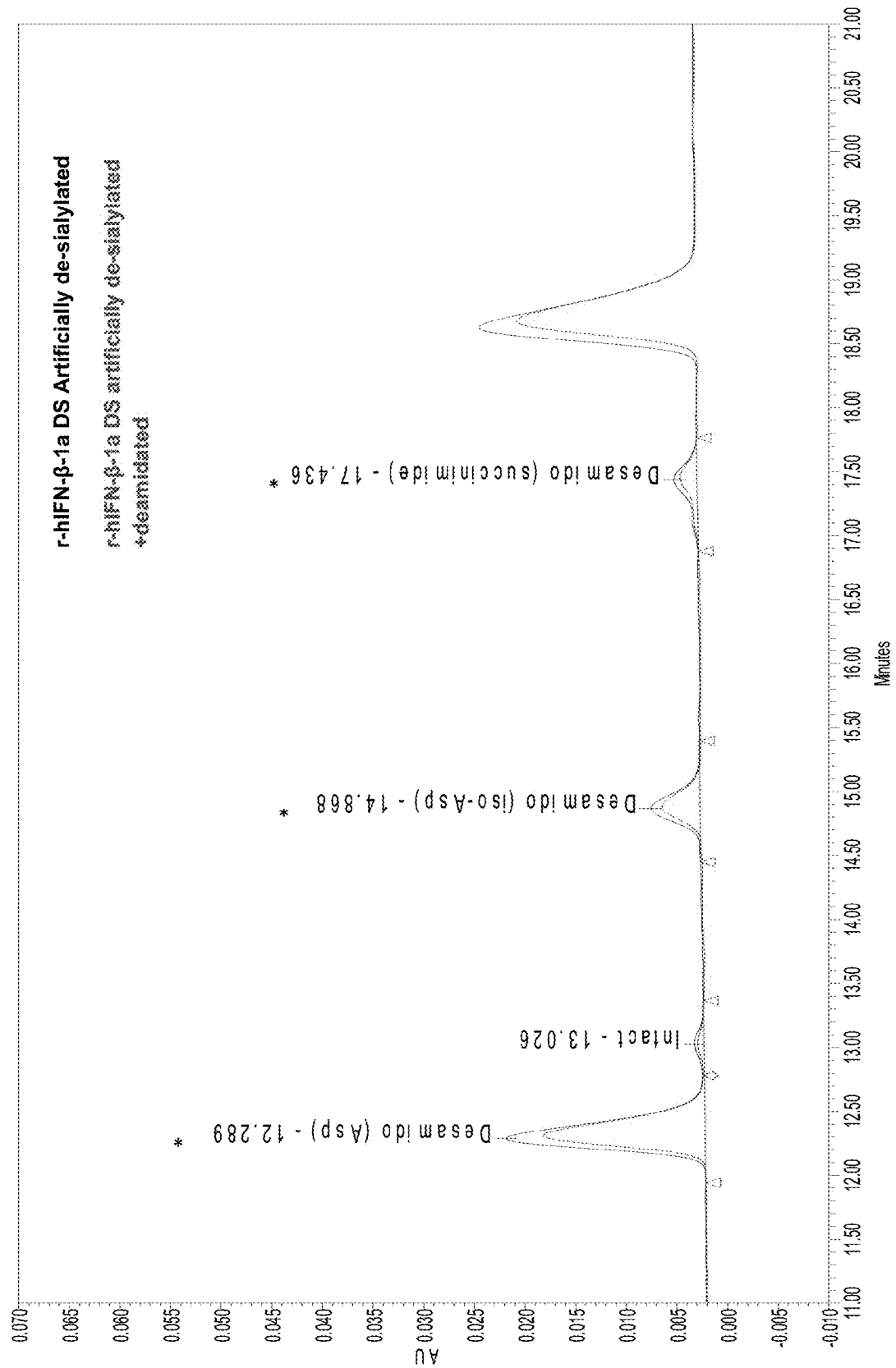
FIGS. 8A and B Deamidation Level of IFN-beta 1a artificially de-sialylated and artificially deamidated and de-sialylated IFN-beta 1a in an Overlay.

As shown in FIGS. 3 to 8, there is an evident change in the peak abundance related to deamidated species. This observation has been confirmed and quantified in the Table below.

TABLE 2

| Deamidation level by peptide mapping/UPLC | |
|---|---|
| Sample Name | Desamido % |
| IFN-β-1a DS artificially deamidated | 96.76 |
| IFN-β-1a DS artificially deamidated and de-sialylated | 96.67 |
| IFN-β-1a DS artificially de-sialylated | 18.00 |
| IFN-β-1a DS untreated | 17.32 |

As reported in Table above, it has been clearly demonstrated that the deamidation treatment applied ensures almost complete IFN-β-1a deamidation with a level of nearly 97%. In addition, de-sialylation treatment does not alter the deamidation level with respect to the untreated sample.

3. Results on Biological Characterization

The results relative to the MHC class I expression as well as antiviral activity are reported in the present sections.

3.1 MHC Class I Expression by Immunomodulatory Bioassay

The immunomodulatory assay is based on the capability of IFN-ß-1a to up regulate the MHC class I expression in A549 cells in a dose related manner. The expression of MHC class I is detected by flow cytometry using a specific fluorescent labelled antibody.

Briefly, A549 cells (32,000 cells/well) were incubated with 12 different concentrations of IFN-ß-1a ranging from 0.000381 ng/mL up to 1600 ng/mL for 48 hours at 37° C., 5% $CO_2$. In order to evaluate the basal expression level of MHC class I, untreated cells were run as well. Then, cells were harvested and the expression of MHC class I was evaluated by FACS analysis using a FITC-conjugated anti-hMHC class I antibody. FACS analysis was performed according to the internal procedure.

The dose response curve of the reference and samples are fitted by 4PL algorithm and the concentration able to lead to 50% of the maximum possible expression ($EC_{50}$) is automatically calculated.

Results are expressed as activity percentage with respect to the reference material on the basis of the $EC_{50}$ values. For each sample, results are the average of three independent assays performed over three different weeks and each of which is composed by two independent runs (a total of 6 analytical runs).

Before calculating the biological activity, the biological behaviour of all samples was checked as shown in FIG. 9.

The dose-response curves of all samples had a comparable upper and lower plateau and slope such demonstrating the curve similarity necessary for further evaluation. Potency values are reported in FIG. 10 together with a graphical representation for a better understanding of the differences.

The data reported in FIG. 10 above show an up-regulation of the MHC class I expression mediated by IFN-ß-1a deamidated samples compared to the IFN-ß-1a untreated and the IFN-ß-1a de-sialylated. Concluding from the data obtained, the deamidation process leads to an IFN-ß-1a with a double capability acquired to up-regulate the expression of its biological endpoint revealed. This result is evident comparing the IFN-ß-1a deamidated versus the IFN-ß-1a untreated as well as the IFN-ß-1a deamidated/de-sialylated versus the IFN-ß-1a de-sialylated. It can be seen that deamidation-dependent increase in biological activity is dependent on sialylation of IFN-beta 1a.

3.2 Antiviral Activity by A549/EMCV System

The antiviral activity of IFN-beta-1a was evaluated measuring the protection exerted by the IFN-beta-1a on A549 cells against the cytopathic effect of Encephalomyocarditis virus (EMCV). A brief description of the method is shown below.

A549 cells were plated (40,000 cells/well) in a 96-well microtiter plate containing IFN-beta-1a in a concentration range from 0.016 ng/ml up to 2 ng/ml and then incubated for 20 hours at 37° C., 5% $CO_2$. At the end of the incubation time, EMCV suspension was added in each well. After about 24 hours of incubation at 37° C., 5% $CO_2$, ATPLite 1 Step was added and the cps were measured in each well by a luminometer microplate reader to assess the proliferation and the vitality of the cells.

The dose response curve of the reference and samples is fitted by 4PL algorithm and the concentration able to lead to 50% of the maximum possible expression ($EC_{50}$) is automatically calculated.

Results are expressed as activity percentage with respect to the reference material on the basis of the $EC_{50}$ values. For each sample, results are the average of three independent assays performed over three different days.

Before calculating the biological activity, the biological behavior of all samples was checked as shown in FIG. 11.

The potency values measuring the biological activity of each IFN-ß-1a sample tested were evaluated on the basis of the $EC_{50}$ collected, as percentage ratio between the $EC_{50}$ RHS IFN-ß-1a and the $EC_{50}$ of each sample tested (% estimated relative potency). The experiments were performed independently in a number of n=2 times and the CV % (Coefficient of Variance) was calculated. Results are shown in FIG. 12.

The data stated in FIG. 12 show a higher antiviral activity in A549 cells mediated by IFN-ß-1a deamidated samples compared to the IFN-ß-1a untreated.

Starting from the data obtained, the deamidation process leads to an IFN-ß-1a with a higher capability acquired to increase the biological response revealed. Contrarily, this deamidated feature cannot be seen in IFN-ß-1a deamidated/de-sialylated sample when compared to the IFN-ß-1a de-sialylated, the deamidation process in this case is not able to rescue the effect of the de-sialylated process on the biological activity.

The invention claimed is:

1. A method of deamidating a protein, comprising:
   (a) incubating the protein to be deamidated under alkaline conditions for 16 to 24 hours; and
   (b) purifying the deamidated protein, wherein said protein is IFN-beta or IFN-beta 1 and wherein said incubation is conducted at a pH of 8.9 to 9.5 and at a temperature of 20° C. to 25° C.

2. The method according to claim 1, wherein said purification comprises ultra-filtration.

3. The method according to claim 1, said method comprising incubating the protein to be deamidated under alkaline conditions for 20 hours.

4. The method according to claim 1, wherein said protein is IFN-beta.

5. The method according to claim 1, wherein said protein is IFN-beta 1.

* * * * *

SEQUENCE LISTING

```
<160> NUMBER OF SEQ ID NOS: 2

<210> SEQ ID NO 1
<211> LENGTH: 166
<212> TYPE: PRT
<213> ORGANISM: Homo sapiens

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
```

```
                    100                 105                 110
Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 166
<212> TYPE: PRT
<213> ORGANISM: Artificial Sequence
<220> FEATURE:
<223> OTHER INFORMATION: deamidated IFN-beta 1a
<220> FEATURE:
<221> NAME/KEY: MOD_RES
<222> LOCATION: (25)..(25)
<223> OTHER INFORMATION: Xaa is aspartate, isoaspartate or succinimide

<400> SEQUENCE: 2

Met Ser Tyr Asn Leu Leu Gly Phe Leu Gln Arg Ser Ser Asn Phe Gln
1               5                   10                  15

Cys Gln Lys Leu Leu Trp Gln Leu Xaa Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```